(12) United States Patent
Manchem et al.

(10) Patent No.: US 12,257,234 B2
(45) Date of Patent: Mar. 25, 2025

(54) METHODS OF TREATING FIBROTIC LIVER DISEASES OR CONDITIONS WITH INDEGLITAZAR

(71) Applicant: PLEIOGENIX INC., Carlsbad, CA (US)

(72) Inventors: Prasad Manchem, Carlsbad, CA (US); Joseph L. Evans, Saint Louis, MO (US)

(73) Assignee: PLEIOGENIX INC., Carlsbad, CA (US)

( * ) Notice: Subject to any disclaimer, the term of this patent is extended or adjusted under 35 U.S.C. 154(b) by 0 days.

(21) Appl. No.: 18/771,595

(22) Filed: Jul. 12, 2024

(65) Prior Publication Data

US 2025/0017901 A1 Jan. 16, 2025

Related U.S. Application Data

(60) Provisional application No. 63/532,001, filed on Aug. 10, 2023, provisional application No. 63/526,840, filed on Jul. 14, 2023.

(51) Int. Cl.

| *A61K 31/404* | (2006.01) |
| *A61K 31/522* | (2006.01) |
| *A61K 31/53* | (2006.01) |
| *A61K 31/573* | (2006.01) |
| *A61P 1/16* | (2006.01) |

(52) U.S. Cl.
CPC .......... *A61K 31/404* (2013.01); *A61K 31/522* (2013.01); *A61K 31/53* (2013.01); *A61K 31/573* (2013.01); *A61P 1/16* (2018.01)

(58) Field of Classification Search
CPC ................................ A61K 31/404; A61P 1/16
See application file for complete search history.

(56) References Cited

U.S. PATENT DOCUMENTS

| 7,202,266 | B2 | 4/2007 | Arnold | |
| 11,241,420 | B2 | 2/2022 | Ciccocioppo | |
| 2005/0288354 | A1* | 12/2005 | Arnold | C07D 401/12 548/494 |
| 2006/0252670 | A1 | 11/2006 | Fiorucci | |
| 2007/0072904 | A1 | 3/2007 | Lin | |
| 2020/0000772 | A1 | 1/2020 | Lefebvre | |
| 2023/0109432 | A1 | 4/2023 | Gillberg | |

FOREIGN PATENT DOCUMENTS

| CN | 115504925 A | 12/2022 |
| EP | 2990037 A1 | 3/2016 |
| WO | 2005009958 A1 | 2/2005 |

OTHER PUBLICATIONS

Artis et al. PNAS, Jan. 6, 2009, vol. 106, No. 1, p. 262-267 (Year: 2009).*
Gul, et al., Deciphering the relational dynamics of AF-2 domain of PAN PPAR through drug repurposing and comparative simulations, PLOS ONE, (2023), p. 1-35.
Francque, et al., A randomized, controlled trial of the pan-PPAR agonist lanifibranor in NASH, New England Journal of Medicine, (2021), 385:1547-1558.
Pawlak, et al., Molecular mechanism of PPARα action and its impact on lipid metabolism, inflammation and fibrosis in non-alcoholic fatty liver disease, Journal of Hepatology, (2015), 62:720-733.
Barbosa-Da-Silva, et al., Singular effects of PPAR agonists on nonalcoholic fatty liver disease of diet-induced obese mice, Life Sciences, (2015), 127:73-81.
Chen et al., Design, synthesis, and biological evaluation of deuterated indolepropionic acid derivatives as novel long-acting pan PPARα/γ/δ agonists, Bioorganic & Medicinal Chemistry, (2023), 96:117533, p. 1-12.
English translation of CN115504925. Published Dec. 23, 2022.
Cheng et al., Exploration and Development of PPAR modulators in Health and Disease: An Update of Clinical Evidence. Int. J. Mol. Sci., (2019), 20:5055, p. 1-50.
Dolgin, NASH therapies head toward landmark approval, Nature Biotechnology, (2023), 41:587-590.
Kersten et al., The role and regulation of the peroxisome proliferator activated receptor alpha in human liver, Biochimie, (2017), 136:75-84.
International Search Report from Appl. No. PCT/US2024/037827, mail on Sep. 19, 2024.
Artis et al., Scaffold-based discovery of indeglitazar, a PPAR pan-active anti-diabetic agent, PNAS, (2009), 106:262-267.

* cited by examiner

*Primary Examiner* — James D. Anderson
(74) *Attorney, Agent, or Firm* — Nevrivy Patent Law Group P.L.L.C.

(57) ABSTRACT

The present invention relates to methods of treating alcoholic hepatitis in a subject, comprising administering to the subject a therapeutically effective amount of indeglitazar or a pharmaceutically acceptable salt thereof.

22 Claims, 18 Drawing Sheets

METHODS OF TREATING FIBROTIC LIVER DISEASES OR CONDITIONS WITH INDEGLITAZAR

CROSS-REFERENCE TO RELATED APPLICATIONS

This application claims the benefit of U.S. Provisional Appl. No. 63/526,840, filed on Jul. 14, 2023, and U.S. Provisional Appl. No. 63/532,001, filed Aug. 10, 2023, the contents of which are hereby incorporated by reference in their entireties.

FIELD OF THE INVENTION

The field of the invention relates to pharmaceuticals and medicine, in particular to compositions and methods to treat fibrotic conditions of the liver, such as alcoholic hepatitis and non-alcoholic steatohepatitis (NASH), along with other liver disorders.

BACKGROUND

Alcoholic Hepatitis (AH) is a deadly liver disease associated with heavy alcohol consumption, affecting 34% of hospitalized heavy alcohol drinkers (Barrio et al., Alcohol Clin Exp Res., (2004), 28:131-6), and with a mortality rate of 70% within 6 months from the first hospitalization (Moreau R et al., Gastroenterology, (2013), 144:1426-37, 37 el-9). Estimates predict nearly 30,000 people in the U.S. with first hospitalizations for AH annually and a total annual U.S. health care cost of $2.2 Billion (Morgan T R et al., Gastroenterology, (2000), 119:1787-91). The high mortality rate of AH is largely due to a lack of effective treatments (Bataller R et al., N Engl J Med, (2022), 387:2436-48). Alcohol-induced damage to hepatocytes triggers the production of tumor necrosis factor-$\alpha$ (TNF-$\alpha$) (Morgan T R et al., Gastroenterology, (2000), 119:1787-91), interleukin (IL)-1, IL-4, IL-6, IL-13, and IL-8, which attract neutrophils, macrophages, and stellate cells causing liver inflammation, fibrosis, steatosis, and ballooning (Tilg H et al., Hepatology, (2016), 64:955-65; Crews F T et al., Alcohol Clin Exp Res, (2006), 30:720-30; Lucey M R et al., N Engl J Med, (2009), 360:2758-69; Rao R K et al., Am J Physiol Gastrointest Liver Physiol, (2004), 286:G881-4). Attempts to treat AH patients with known immunomodulatory agents, such as corticosteroids or pentoxifylline, have failed to improve overall survival or to decrease liver damage (Rao R K et al., Am J Physiol Gastrointest Liver Physiol, (2004), 286:G881-4; Thursz M et al., Health Technol Assess, (2015), 19:1-104; Du J et al., World J Gastroenterol, (2014), 20:569-77). Moreover, corticosteroids are linked to severe side effects, and AH patients that develop infections after corticosteroid treatment have a higher mortality rate (Yasir M et al., StatPearls. Treasure Island (FL): StatPearls Publishing-Copyright © 2023, StatPearls Publishing LLC., (2023)); Louvet A et al., Gastroenterology, (2009), 137:541-8). Currently, the only effective cure for AH is early orthotopic liver transplantation (OLT) (Mathurin et al., N Engl J Med, (2011), 365:1790-800; Jesudian A B et al., Curr Opin Organ Transplant, (2016), 21:107-10). Unfortunately, OLT is not easily accessible, is extremely expensive ($430,000), and requires life-long immunosuppression associated with long-term side effects (Thompson J A et al., Alcohol, (2018), 71:57-63; Tasdogan B E et al., Euroasian J Hepatogastroenterol, (2019), 9:96-101).

Non-alcoholic fatty liver disease (NAFLD) is a condition in which excess fat is stored in an individual's liver. NAFLD is generally divided into two separate subtypes, known as "simple fatty liver" and non-alcoholic steatohepatitis (NASH) (Pouwels S, et al., BMC Endocr Disord, 2022; 22(1):63; Sheka A C et al., JAMA. 2020; 323(12):1175-83). NASH is a severe form of NAFLD in which the patient has hepatitis—inflammation of the liver—and liver cell damage, in addition to fat accumulation in the liver (i.e. steatosis). Inflammation and liver cell damage can cause fibrosis (i.e. scarring) of the liver. NASH may also lead to cirrhosis or liver cancer (Sheka A C et al., JAMA. 2020; 323(12):1175-83).

NAFLD may be differentiated from NASH by the NAFLD Activity Score (NAS), the sum of the histopathology scores of a liver biopsy for steatosis (0 to 3), lobular inflammation (0 to 2), and hepatocellular ballooning (0 to 2). A NAS of <3 corresponds to NAFLD, 3-4 corresponds to borderline NASH, and ≥5 corresponds to NASH. The biopsy is also scored for fibrosis (0 to 4).

Between 30 and 40 percent of adults in the United States (~100 million) have NAFLD (Foundation AL. Nonalcoholic Fatty Liver Disease (NAFLD) 2023. Available from: https://liverfoundation.org/liver-diseases/fatty-liver-disease/nonalcoholic-fatty-liver-disease-nafld/). Weight loss is currently the primary method recommended for treating NAFLD and NASH (Pouwels S, et al., BMC Endocr Disord, 2022; 22(1):63; Sheka A C et al., JAMA. 2020; 323(12):1175-83). Weight loss can reduce fat in the liver, inflammation, and fibrosis. A study by the National Institute of Diabetes and Digestive and Kidney Diseases' NASH Clinical Research Network External link found that treatment with vitamin E or pioglitazone improved NASH in about half of the people treated (Sanyal A J et al., N Engl J Med, (2010), 362:1675-85).

Pioglitazone selectively stimulates the nuclear receptor peroxisome proliferator-activated receptor gamma (PPAR-$\gamma$) and to a lesser extent PPAR-$\alpha$ (Devchand P R et al., Front Pharmacol, (2018), 9:1093). It modulates the transcription of the genes involved in the control of glucose and lipid metabolism in the muscle, adipose tissue, and the liver. As a result, pioglitazone reduces insulin resistance in the liver and peripheral tissues, decreases gluconeogenesis in the liver, and reduces the quantity of glucose and glycated hemoglobin in the bloodstream. Pioglitazone also suffers from serious side effects, including upper respiratory tract infection, edema, hypoglycemia, cardiac failure, exacerbation of congestive heart failure, bone fracture, headache, and pharyngitis. The largest incidence of edema has been reported when pioglitazone is used in combination with insulin. In clinical studies, these patients have an incidence of edema of 15.3% when treated with insulin plus pioglitazone (compared with 7.0% in the insulin-only groups, respectively) (Mudaliar S et al., Endocr Pract, (2003), 9:406-16).

Indeglitazar is an orally available pan peroxisome proliferator activated receptor (PPAR) agonist, first described in U.S. Pat. No. 7,202,266, to Plexxikon, Inc. (Berkeley, CA; acquired by Daichi Sankyo (Japan) in 2022 and subsequently closed). Indeglitazar was first developed for type 2 diabetes (T2D), and its safety has been extensively evaluated in multiple non-clinical trials and in Phase I (NCT00448032) and Phase 2A and B (NCT00425919) clinical trials. Indeglitazar has been identified from a low-molecular weight small-molecule library, coupling low-affinity biochemical screening with high-throughput co-crystallography, and optimized to selectively modulate the activities of all three PPAR isoforms (Artis D R et al., Proc Natl Acad Sci USA, (2009), 106:262-7). Indeglitazar displays full agonism against PPARα and partial agonism towards PPARδ and PPARγ (Artis D R et al., Proc Natl Acad Sci USA, (2009), 106:262-7). Indeglitazar also overcomes side effects (e.g. edema, weight gain, fractures) associated with full PPARγ activation (Betteridge D J et al., Diabet Med, (2011), 28:759-71; Nesto R W et al., Circulation, (2003), 108:2941-8).

Compared with full PPAR γ-agonists like pioglitazone, indeglitazar is reportedly less potent in promoting adipocyte differentiation and only partially effective in stimulating adiponectin gene expression. Indeglitazar was first developed for type-2 diabetes, and its safety has been extensively evaluated in multiple non-clinical trials and in Phase I (NCT00448032) and Phase 2A and B (NCT00425919) clinical trials. The compound has demonstrated beneficial effects in vivo on glucose, triglycerides, cholesterol, body weight, and other metabolic parameters (Artis D R et al., Proc Natl Acad Sci USA, (2009), 106:262-7).

What is needed are new therapeutics that are safe and efficacious for the treatment of fibrotic liver conditions or diseases, including alcoholic hepatitis, non-alcoholic fatty liver disease, non-alcoholic steatohepatitis and fibrosis. What is especially needed are molecules that are capable of treating the ballooning, inflammation, reduced liver function, and fibrosis that are characteristic of NAFLD, NASH, alcoholic hepatitis and other conditions in the liver.

The foregoing description of the background is provided to aid in understanding the invention and is not admitted to be or to describe prior art to the invention.

SUMMARY OF THE INVENTION

It is to be understood that both the present general description of the invention and the following detailed description are exemplary, and thus do not restrict the scope of the invention.

This invention is based on the discovery of a therapy for the treatment of certain fibrotic liver diseases or conditions or diseases that may lead to hepatic fibrosis, including alcoholic hepatitis, non-alcoholic fatty liver disease, non-alcoholic steatohepatitis and other fibrotic conditions in liver by administration of effective amounts of indeglitazar, a non-thiazolidinedione pan-PPAR agonist.

In one aspect, the invention provides a method of treating a fibrotic liver disease or condition in a subject, comprising administering to the subject a therapeutically effective amount of indeglitazar or a pharmaceutically acceptable salt thereof. In some embodiments, the method further comprises administering to the subject one or more additional therapies to treat alcoholic hepatitis. In some embodiments, the one or more therapies comprises effective amounts of prednisolone or pentoxifylline.

In another aspect, the invention provides a method of treating alcoholic hepatitis in a subject, comprising administering to the subject a therapeutically effective amount of indeglitazar or a pharmaceutically acceptable salt thereof. In some embodiments, the method further comprises administering to the subject one or more additional therapies to treat alcoholic hepatitis. In some embodiments, the one or more therapies comprises effective amounts of prednisolone or pentoxifylline.

In another aspect, the invention provides a method of treating hepatic steatosis in a subject, comprising administering to the subject a therapeutically effective amount of indeglitazar or a pharmaceutically acceptable salt thereof. In some embodiments, the method further comprises administering to the subject one or more therapies to treat hepatic steatosis. In some embodiments, the one or more therapies comprises an effective amount of an agent to promote weight loss in the subject. In some embodiments, the one or more therapies comprises dieting, exercise, or a combination thereof.

In another aspect, the invention provides a method of treating non-alcoholic fatty liver disease in a subject, comprising administering to the subject a therapeutically effective amount of indeglitazar or a pharmaceutically acceptable salt thereof. In some embodiments, the method further comprises administering to the subject one or more therapies to treat non-alcoholic fatty liver disease. In some embodiments, the one or more therapies comprises an effective amount of an agent to promote weight loss in the subject. In some embodiments, the one or more therapies comprises dieting, exercise, or a combination thereof.

In another aspect, the invention provides a method of treating non-alcoholic steatohepatitis in a subject, comprising administering to the subject a therapeutically effective amount of indeglitazar or a pharmaceutically acceptable salt thereof. In some embodiments, the method further comprises administering to the subject one or more therapies to treat non-alcoholic steatohepatitis. In some embodiments, the one or more therapies comprises an effective amount of an agent to promote weight loss in the subject. In some embodiments, the one or more therapies comprises dieting, exercise, or a combination thereof.

In another aspect, the invention provides a method of treating hepatic fibrosis in a subject, comprising administering to the subject a therapeutically effective amount of indeglitazar or a pharmaceutically acceptable salt thereof. In some embodiments, the method further comprises administering to the subject one or more therapies to treat hepatic fibrosis. In some embodiments, the one or more therapies comprises an effective amount of an agent to promote weight loss in the subject. In some embodiments, the one or more therapies comprises dieting, exercise, or a combination thereof.

In another aspect, the invention provides a method of increasing adiponectin in a subject, comprising administering to the subject a therapeutically effective amount of indeglitazar or a pharmaceutically acceptable salt thereof. In some embodiments, the method further comprises administering to the subject one or more therapies to treat alcoholic hepatitis. In some embodiments, the one or more therapies comprises effective amounts of prednisolone or pentoxifylline.

In another aspect, the invention provides a method of improving liver enzyme function by reducing aspartate aminotransferase (AST) and/or alanine aminotransferase (ALT) activity in liver of a subject, comprising administering to the subject a therapeutically effective amount of indeglitazar or a pharmaceutically acceptable salt thereof. In some embodiments, the method further comprises administering to the subject one or more therapies to treat alcoholic hepatitis. In some embodiments, the one or more therapies comprises effective amounts of prednisolone or pentoxifylline.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION

Figure 1:
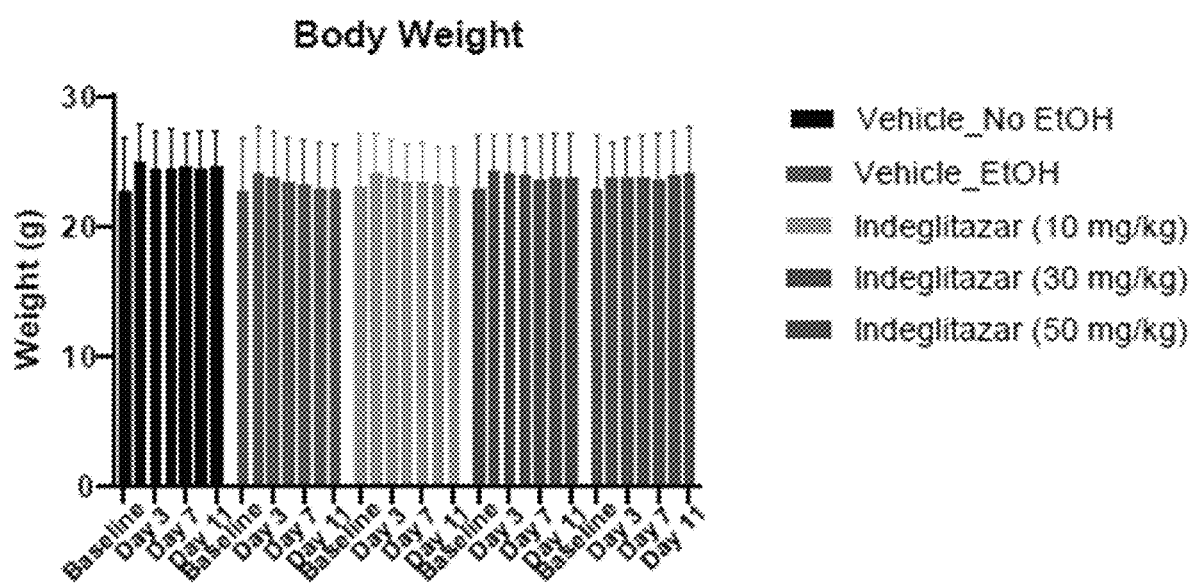
FIG. 1. A dose response (10, 30, and 50 mg/kg/day) of indeglitazar showing that indeglitazar has no significant effect on body weight in the ethanol-treated mouse (male and female mice) model of human AH described in Example 1.

Reference will now be made in detail to embodiments of the invention which, together with the drawings and the following examples, serve to explain the principles of the invention. These embodiments are described in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). As used in this specification and in the claims which follow, the singular forms "a," "an" and "the" include plural references unless the context clearly dictates otherwise. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of."

It is contemplated that any method or composition described herein can be implemented with respect to any other method or composition described herein.

"Therapeutically effective amount" means that amount which, when administered to a subject such as a human for supporting or affecting a metabolic process, or for treating or preventing a disease, is sufficient to cause such treatment or prevention of the disease, or supporting or affecting the metabolic process. As used herein, the terms "effective amount" or "therapeutically effective amount" are interchangeable and refer to an amount that results in an improvement or remediation of at least one symptom of the disease or condition. Those of skill in the art understand that the effective amount may improve the patient's or subject's condition but may not be a complete cure of the disease and/or condition.

When ranges are given by specifying the lower end of a range separately from the upper end of the range, or specifying particular numerical values, it will be understood that a range can be defined by selectively combining any of the lower end variables, upper end variables, and particular numerical values that is mathematically possible. In like manner, when a range is defined as spanning from one endpoint to another, the range will be understood also to encompass a span between and excluding the two endpoints.

When "drug therapy" or a "method of treatment" or "method of treating" is recited, it will be understood that the therapy can be accomplished through any suitable route of administration using any acceptable dosage form, and that the drug can be administered as the free base, a salt, or an ester or other prodrug moiety.

When used herein the term "about" will compensate for variability allowed for in the pharmaceutical industry and inherent in products in this industry, such as differences in product strength due to manufacturing variation and time-induced product degradation, salt selection, and molecular solvates and degrees of hydration. As used herein, under such circumstances, the term "about" means at most plus or minus 10% of the numerical value of the number with which it is being used.

The terms "treating" and "treatment" as used herein refer to administering to a subject a therapeutically effective amount of a composition so that the subject has an improvement in a disease or condition. An improvement is any observable or measurable improvement. Thus, one of skill in the art realizes that a treatment may improve the patient's condition, but may not be a complete cure of the disease. In other words, in the context of the present invention insofar as it relates to any of the diseases or conditions recited herein, the term "treatment" means to reduce the occurrence of a symptom or condition, or to relieve or alleviate at least one symptom associated with such condition, or to slow or reverse the progression of such condition, or to manage or affect the metabolic processes underlying such condition. Within the meaning of the present invention, the terms also denote to arrest, delay the onset (i.e., the period prior to clinical manifestation of a disease) and/or reduce the risk of developing or worsening a disease. Thus, treating may also comprise treating subjects at risk of developing a disease and/or condition. In some embodiments, treatment encompasses demonstration of resolution of NASH and/or improvement in fibrosis score based on liver biopsy; reduction of the incidence of progression to cirrhosis, hepatocellular carcinoma, and/or other liver-related outcomes; reduction or improvement in imaging based on serum levels or indicators of nonalcoholic steatohepatitis activity; reduction or improvement in non-alcoholic steatohepatitis disease activity; or a reduction in the medical consequences of non-alcoholic steatohepatitis.

The phrase "acceptable" as used in connection with compositions of the invention, refers to molecular entities and other ingredients of such compositions that are physiologically tolerable and do not typically produce untoward reactions when administered to a subject (e.g., a mammal such as a human).

The terms "hepatic" and "liver" are used interchangeably herein.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject. In some embodiments, the subject is a human.

Figure 18:
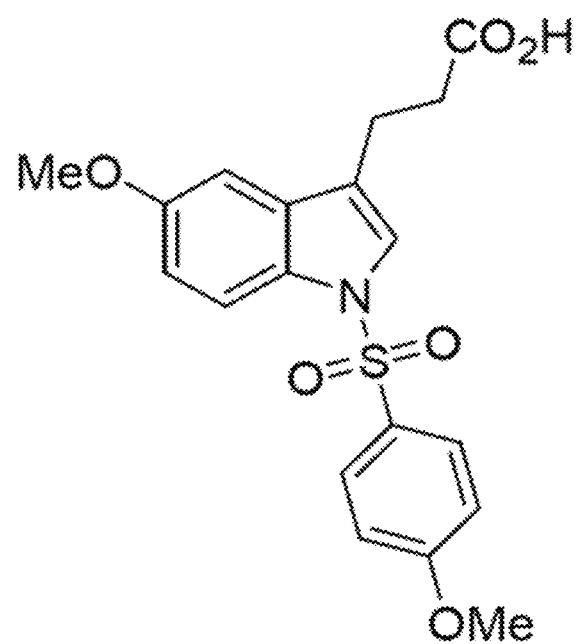
FIG. 18. Chemical structure of indeglitazar.

"Indeglitazar" is a compound having the chemical name 3-[5-methoxy-1-(4-methoxybenzenesulfonyl)-1H-indol-3-yl]-propanoic acid. The molecular formula is shown in FIG. 18. Indeglitazar is also referred to herein as PLG888.

NAFLD or hepatic steatosis (fatty liver) can also be referred to as MASLD (metabolic dysfunction-associated steatotic liver disease) or MAFLD (metabolic dysfunction-associated fatty liver disease).

NASH can also be referred to as MASH (metabolic dysfunction-associated steatohepatitis).

When percentages are given herein, it will be understood that the percentages are weight percent, and that proportions are based on weight, unless otherwise stated to the contrary or evident from the surrounding context.

Wherever an analysis or test is required to understand a given property or characteristic recited herein, it will be understood that the analysis or test is performed in accordance with applicable guidance, draft guidances, regulations and monographs of the United States Food and Drug Administration ("FDA"), Lab Protocols for NHANES data published by the United States Centers for Disease Control, and United States Pharmacopoeia ("USP") applicable to drug products in the United States in force as of Jan. 1, 2020, unless otherwise specified.

In one embodiment, the invention provides a method of treating a fibrotic liver disease or condition in a subject, comprising administering to the subject a therapeutically effective amount of indeglitazar or a pharmaceutically acceptable salt thereof. In some embodiments, indeglitazar is administered either alone or in combination one or more other therapies, such as administration with prednisolone or pentoxifylline, an agent that promotes weight loss, or a diet or exercise regimen. In some embodiments, the subject is human and does not have type 2 diabetes.

The fibrotic liver disease or condition is not particularly limiting. Fibrotic liver diseases or conditions as used herein refers to diseases or conditions where hepatic fibrosis is present and diseases or conditions that can ultimately lead to hepatic fibrosis being present. In some embodiments, the disease or condition is selected from the group consisting of alcoholic hepatitis, hepatic fibrosis, non-alcoholic fatty liver disease, non-alcoholic steatohepatitis, chronic kidney disease, a pulmonary fibrotic disorder, systemic scleroderma, and primary biliary cirrhosis.

In some embodiments, the disease or condition is fatty liver. In some embodiments, the disease or condition is non-alcoholic fatty liver disease. In some embodiments, the disease or condition is non-alcoholic steatohepatitis. In some embodiments, the disease or condition is non-alcoholic steatohepatitis with liver fibrosis. In some embodiments, the disease or condition is nonalcoholic steatohepatitis with cirrhosis. In some embodiments, the disease or condition is non-alcoholic steatohepatitis with cirrhosis and hepatocellular carcinoma. In some embodiments, the disease or condition is non-alcoholic steatohepatitis with cirrhosis and metabolic-related diseases.

In some embodiments, the invention provides a method of treating alcoholic hepatitis in a subject, comprising administering to the subject a therapeutically effective amount of indeglitazar or a pharmaceutically acceptable salt thereof. In some embodiments, indeglitazar is administered either alone or in combination one or more other therapies, such as administration with prednisolone or pentoxifylline, an agent that promotes weight loss, or a diet or exercise regimen. In some embodiments, the subject is human and does not have type 2 diabetes.

In some embodiments, the invention provides a method of treating hepatic steatosis in a subject, comprising administering to the subject a therapeutically effective amount of indeglitazar or a pharmaceutically acceptable salt thereof. In some embodiments, indeglitazar is administered either alone or in combination one or more other therapies, such as administration with prednisolone or pentoxifylline, an agent that promotes weight loss, or a diet or exercise regimen. In some embodiments, the subject is human and does not have type 2 diabetes.

In another aspect, the invention provides a method of treating non-alcoholic fatty liver disease in a subject, comprising administering to the subject a therapeutically effective amount of indeglitazar or a pharmaceutically acceptable salt thereof. In some embodiments, indeglitazar is administered either alone or in combination one or more other therapies, such as administration with prednisolone or pentoxifylline, an agent that promotes weight loss, or a diet or exercise regimen. In some embodiments, the subject is human and does not have type 2 diabetes.

In another aspect, the invention provides a method of treating non-alcoholic steatohepatitis in a subject, comprising administering to the subject a therapeutically effective amount of indeglitazar or a pharmaceutically acceptable salt thereof. In some embodiments, indeglitazar is administered either alone or in combination one or more other therapies, such as administration with prednisolone or pentoxifylline, an agent that promotes weight loss, or a diet or exercise regimen. In some embodiments, the subject is human and does not have type 2 diabetes.

In another aspect, the invention provides a method of treating hepatic fibrosis in a subject, comprising administering to the subject a therapeutically effective amount of indeglitazar or a pharmaceutically acceptable salt thereof. In some embodiments, indeglitazar is administered either alone or in combination one or more other therapies, such as administration with prednisolone or pentoxifylline, an agent that promotes weight loss, or a diet or exercise regimen. In some embodiments, the subject is human and does not have type 2 diabetes.

In some embodiments, the invention provides a method of increasing adiponectin in a subject, comprising administering to the subject a therapeutically effective amount of indeglitazar or a pharmaceutically acceptable salt thereof. In some embodiments, the subject has a disease or condition selected from the group consisting of alcoholic hepatitis, hepatic fibrosis, non-alcoholic fatty liver disease, non-alcoholic steatohepatitis, chronic kidney disease, a pulmonary fibrotic disorder, systemic scleroderma, and primary biliary cirrhosis. In some embodiments, indeglitazar is administered either alone or in combination one or more other therapies, such as administration with prednisolone or pentoxifylline, an agent that promotes weight loss, or a diet or exercise regimen. In some embodiments, indeglitazar or a pharmaceutically acceptable salt thereof is administered in combination with the standard of care for treating human NAFLD, NASH, or liver fibrosis (e.g., weight loss). In some embodiments, the subject is human and does not have type 2 diabetes.

In some embodiments, the invention provides a method of improving liver enzyme function by reducing aspartate aminotransferase (AST) and/or alanine aminotransferase (ALT) activity in liver of a subject, comprising administering to the subject a therapeutically effective amount of indeglitazar or a pharmaceutically acceptable salt thereof. In some embodiments, the subject has a disease or condition selected from the group consisting of alcoholic hepatitis, hepatic fibrosis, non-alcoholic fatty liver disease, non-alcoholic steatohepatitis, chronic kidney disease, a pulmonary fibrotic disorder, systemic scleroderma, and primary biliary cirrhosis. In some embodiments, indeglitazar is administered either alone or in combination one or more other therapies, such as administration with prednisolone or pentoxifylline, an agent that promotes weight loss, or a diet or exercise regimen. In some embodiments, the subject is human and does not have type 2 diabetes.

In some embodiments, the invention provides a method of increasing survival time in a subject having a fibrotic disease or condition, comprising administering to the subject a therapeutically effective amount of indeglitazar or a pharmaceutically acceptable salt thereof. In some embodiments, the subject has a disease or condition selected from the group consisting of alcoholic hepatitis, hepatic fibrosis, non-alcoholic fatty liver disease, non-alcoholic steatohepatitis, chronic kidney disease, a pulmonary fibrotic disorder, systemic scleroderma, and primary biliary cirrhosis. In some embodiments, indeglitazar is administered either alone or in combination one or more other therapies, such as administration with prednisolone or pentoxifylline, an agent that promotes weight loss, or a diet or exercise regimen. In some embodiments, the subject is human and does not have type 2 diabetes.

In some embodiments, indeglitazar or a pharmaceutically acceptable salt thereof is administered according to the methods of the invention in a combination therapy with one or more additional pharmaceutical agents. In some embodiments, the agents are selected from prednisolone, pentoxifylline or a combination thereof. In some embodiments, the agent is an acetyl-CoA carboxylase (ACC) inhibitor, a diacylglycerol O-acyltransferase 1 (DGAT-1) inhibitor, a monoacyl Glycerol O-acyltransferase inhibitor, phosphodiesterase (PDE)-10 inhibitor, AMPK activator, sulfonylurea, meglitinide, α-amylase inhibitor, α-glucoside hydrolase inhibitor, α-glucoside hydrolase inhibitor, PPARγ agonist, PPARα/γ agonist, biguanide, glucagon-like peptide 1 (GLP-1) modulator, liraglutide, albiglutide, exenatide, albiglutide, lixisenatide, dulaglutide, semaglutide, protein tyrosine phosphatase-1B (PTP-1B) inhibitor, SIRT-1 activator, dipeptidyl peptidase IV (DPP-IV) inhibitor, insulin secretagogue, fatty acid oxidation inhibitor, A2 antagonist, c-jun amino-terminal kinase (JNK) inhibitor, glucokinase activator (GKa), insulin, insulin mimetic, glucagon phosphorylase inhibitor, VPAC2 receptor agonist, SGLT2 inhibitor, glucagon receptor modulator, GPR119 modulator, FGF21 derivative or analogue, TGR5 receptor modulator, GPBAR1 receptor modulator, GPR40 agonist, GPR120 modulator, high affinity nicotinic acid receptor (HM74A) activator, SGLT1 inhibitor, carnitine palitoyl transferase inhibitor or modulator, fructose 1,6-diphosphatase inhibitor, aldose reductase inhibitor, mineralocorticoid receptor inhibitor, TORC2 inhibitor, CCR2 and/or CCR5 inhibitor, PKC isoform inhibitor (e.g. PKCa, PKCP, PKCT), fatty acid synthase inhibitor, serine palmitoyl transferase inhibitor, GPR81, GPR39, modulators of GPR43, GPR41 or GPR105, Kv1.3, retinol binding protein 4, glucocorticoid receptor, somatostatin receptor, inhibitor or modulator of PDHK2 or PDHK4, MAP4K4 inhibitor, IL1 family modulator including IL1beta, HMG-CoA reductase inhibitor, squalane synthase inhibitor, fibrate, bile acid sequestrant, ACAT inhibitor, MTP inhibitor, lipid oxygenase inhibitor, cholesterol absorption inhibitor, PCSK9 modulator, cholesteryl ester transfer protein inhibitor and RXR alpha modulator.

In some embodiments, the additional pharmaceutical agent includes cysteamine or a pharmaceutically acceptable salt thereof, cystamine or a pharmaceutically acceptable salt thereof, an antioxidant compound, lecithin, Vitamin B complex, bile salt preparation, cannabinoid-1 (CB1) receptor antagonist, cannabinoid-1 (CB1) receptor inverse agonist, peroxisome proliferator-activated receptor) activity modulator, benzothiazepine, RNA antisense construct for inhibiting protein tyrosine phosphatase (PTPRU), heteroatom-linked and substituted piperidines and their derivatives, azas capable of inhibiting stearoyl-coenzyme alpha delta-9 desaturase, cyclopentane derivatives, acylamide compounds with adiponectin secretion stimulant or inducer activity, quaternary ammonium compounds, glatiramer acetate, pentraxin protein, HMG-CoA reductase inhibitor, n-acetyl cysteine, isoflavone compounds, macrolides selected from the group consisting of antibiotics, galectin inhibitors, antibodies, and any combinations thereof.

In some embodiments, indeglitazar or a pharmaceutically acceptable salt thereof is administered in combination with an anti-diabetic agent. In some embodiments, anti-diabetic agent includes, for example, insulin, metformin, DPPIV inhibitors, GLP-1 receptor agonists, analogs and mimics, SGLT1 and SGLT2 inhibitors. Suitable anti-diabetic agents include acetyl-CoA carboxylase (ACC) inhibitors, diacylglycerol O-acyltransferase 1 (DGAT-1) inhibitors, AZD7687, LCQ908, monoacylglycerol O-acyltransferase inhibitor, phosphodiesterase (PDE)-10 inhibitors, AMPK activators, sulfonylureas (e.g., acetohexamide, chlorpropamide, diabinose, glibenclamide, glipizide, glyburide, glimepiride, gliclazide, glypentide, gliquidone, glyphazole) solamide, tolazamide, tolbutamide, meglitinides, α-amylase inhibitors (e.g., tendamistat, trestatin, and AL-3688), α-glucoside hydrolase inhibitors (e.g., acarbose), α-glucoside hydrolase inhibitors (e.g., adiposin, camiglibose, emiglitate, miglitol, voglibose, pradimycin-Q, and salvostatin), PPARγ agonists (e.g., valaglitazone, ritazone, darglitazone, englitazone, isaglitazone, pioglitazone and rosiglitazone), PPARα/γ agonists (e.g., CLX-0940, GW-1536, GW-1929, GW-2433, KRP-297, L-796449, LR-90, MK-0767 and SB-219994), biguanides (e.g. metformin), glucagon-like peptide 1 (GLP-1) modulators such as agonists (e.g. exendin-3 and exendin-4), liraglutide, albiglutide, exenatide, albiglutide, lixisenatide, dulaglutide, semaglutide, NN-9924, TTP-054, protein tyrosine phosphatase-1B (PTP-1B) inhibitors (e.g., trodusquemin, hirthiosal extract), SIRT-1 activators (e.g., resveratrol, GSK2245840 or GSK184072), dipeptidyl peptidase IV (DPP-IV) inhibitors, sitaagliptin, vildagliptin, aloglitb, dutogliptin, linagliptin and saxagliptin, insulin secretagogue, fatty acid oxidation inhibitor, A2 antagonist, c-jun amino-terminal kinase (JNK) inhibitor, GKA, TTP-399, TTP-355, TTP-547, AZD1656, Arry403, MK-0599, TAK-329, AZD5658 or GKM-001, insulin, insulin mimetic, glucagon phosphorylase inhibitor (e.g. GSK1362885), VPAC2 receptor agonist, SGLT2 inhibitor, dapagliflozin, canagliflozin, empagliflozin, tofogliflozin (CSG452), ertuglifl Rosin, ASP-1941, THR1474, TS-071, ISIS388626, LX4211, glucagon receptor modulators, GPR119 modulators, MBX-2982, GSK1292263, APD597, PSN821, FGF21 derivatives or analogs, GPR40 agonist, TAK-875, GPR120 modulators, high affinity nicotinic acid receptor (HM74A) activators, SGLT1 inhibitors such as GSK1614235, metformin, DPP-IV inhibitors (e.g., sitagliptin, vildagliptin, alogliptin, dutogliptin, linagliptin and saxagliptin), carnitine palitoyl transferase inhibitors or modulators, fructose 1,6-diphosphatase inhibitors, aldose reductase inhibitors, mineralocorticoid receptor inhibitors, TORC2 inhibitors, CCR2 and/or CCR5 inhibitors, fatty acid synthase inhibitors, inhibitors of serine palmitoyl transferase, GPR81, GPR39, GPR43, GPR41 or GPR105 modulators, Kv1.3, retinol binding protein 4, glucocorticoid receptor, somatostatin receptor (e.g., SSTR1, SSTR2, SSTR3 and SSTR5), inhibitors or modulators of PDHK2 or PDHK4, MAP4K4 inhibitors, IL1 family modulators including IL1beta, and RXRalpha modulators.

Suitable anti-obesity or weight loss agents include 11β-hydroxy steroid dehydrogenase-1 (11β-HSD type 1) inhibitors, stearoyl-CoA desaturase-1 (SCD-1) inhibitors, MCR-4 agonists, and cholecystokinin-A (CCK-1), monoamine reuptake inhibitors (e.g. sibutramine), sympathomimetics, β3 adrenergic agonists, dopamine agonists (e.g. bromocriptine), melanocyte-stimulating hormone analogues, 5HT2c agonists, leptin (OB protein), leptin analogs, leptin agonists, galanin antagonists, lipase inhibitors (e.g. tetrahydrolipstatin), anorexiants (e.g. bombesin agonists), neuropeptide-Y Antagonists (e.g., NPY Y5 antagonist), PYY 3-36 (including analogs thereof), thyrometic agents, dehydroepiandrosterone or analogs thereof, glucocorticoid agonists or antagonists, orexin antagonists, glucagon-like peptide-1 agonists, ciliary trophic factors, human agouti-related protein (AGRP) inhibitor, ghrelin antagonist, histamine 3 antagonist or inverse agonist, neuromedin U agonist, MTP/ApoB inhibitor, intestinal-selective MTP inhibitors, opioid antagonists, orexin antagonists, combinations of naltrexone and buprorion, and the like.

In some embodiments, anti-obesity or weight loss agents for use in the combinations of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl), 5-oxo-1-phenyl-4,5-dihydro-2,3,6,10b-tetraaza-benzo[e]azulen-6-yl]-N-isopropyl-acetamide), 5HT2c agonist (e.g., lorcaserin), MCR4 agonists, lipase inhibitors (e.g., cetilistat), PYY 3-36, opioid antagonists (e.g., naltrexone), combinations of naltrexone and buprorion, oleoyl-estrone. (CAS No. 180003-17-2), obinepitide (TM30338), pramlintide, tesofensin (NS2330), leptin, liraglutide, bromocriptine, orlistat, AOD-9604 (CAS No. 221231-10-3), phentermine and topiramate (Qsymia), and sibutramine.

In some embodiments, indeglitazar or a pharmaceutically acceptable salt thereof is administered in a combination therapy with one or more weight loss promoting drugs. In some embodiments, the weight loss promoting drug is a GLP-1 agonist. In some embodiments, the GLP-1 agonist is selected from one or more of tirzepatide, dulaglutide, exenatide, semaglutide, liraglutide, or lixisenatide.

In some embodiments, indeglitazar or a pharmaceutically acceptable salt thereof is administered in a combination therapy with a GIP-1 receptor agonist. In some embodiments, the GIP-1 receptor agonist has dual agonism with both GLP-1 and GIP-1. In some embodiments, the dual agonist is used in combination with indeglitazar or a pharmaceutically acceptable salt thereof to treat NASH.

In some embodiments, indeglitazar or a pharmaceutically acceptable salt thereof is administered in a combination therapy with a glucagon receptor agonist. In some embodiments, the glucagon receptor agonist is a triple agonist with glucagon receptor, GIP-1 and GLP-1. In some embodiments, the triple agonist is used in combination with indeglitazar or a pharmaceutically acceptable salt thereof to treat NASH.

In some embodiments, indeglitazar or a pharmaceutically acceptable salt thereof is administered in a combination therapy with resmetirom (REZDIFFRA). In some embodiments, the combination therapy is used to treat NAFLD or NASH.

In some embodiments, indeglitazar or a pharmaceutically acceptable salt thereof are administered in combination with exercise, a sensible diet, and/or one or more of the additional agents as described herein.

In some embodiments, the methods for treating the fibrotic liver diseases or conditions result in an improvement in a fibrosis marker selected from TIMP metallopeptidase inhibitor-1 ("TIMP-1"), TIMP metallopeptidase inhibitor-2 "(TIMP-2"), hydroxyproline, TGF-β1, hyaluronic acid, type 3 procollagen peptide ("P3NP"), NAFLD fibrosis score ("NFS"), fibrosis-4 ("FIB-4") score, enhanced liver fibrosis ("ELF") score, N-terminal type III collagen pro-peptide ("Pro-C3"), and combinations thereof.

In some embodiments, the treatment methods result in an improvement by one or more grades in the NAS (NAFLD Activity Score). The NAS can range from 0 to 8 and is calculated by the sum of scores of steatosis (0-3), lobular inflammation (0-3) and hepatocyte ballooning (0-2).

In some embodiments, treatment of NASH in accordance with the methods herein result in an improvement in the NAS by one or more grades.

In some embodiments, the treatment methods result in an improvement in liver fibrosis greater than or equal to one stage (NASH CRN fibrosis score) and no worsening of steatohepatitis (defined as no increase in NAS for ballooning, inflammation, or steatosis).

In some embodiments, the methods of treatment result in a reduction of alanine aminotransferase (ALT) activity in liver of a subject. In some embodiments, the magnitude of reduction of ALT is at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%. In some embodiments, the magnitude of reduction of ALT is from about 15% to about 80%, from about 25% to about 70%, or from about 30% to about 60%. In some embodiments, a reduction of ALT results from a method of treating a disease or condition selected from alcoholic hepatitis, hepatic fibrosis, non-alcoholic fatty liver disease, non-alcoholic steatohepatitis, chronic kidney disease, a pulmonary fibrotic disorder, systemic scleroderma, or primary biliary cirrhosis. In some embodiments, the subject is a human. In some embodiments, the method further comprises administering to the subject one or more additional therapies. In some embodiments, the one or more therapies comprises effective amounts of prednisolone, pentoxifylline, or a diet and exercise regimen. In some embodiments, the subject is human and does not have type 2 diabetes.

In some embodiments, the methods of treatment result in a reduction of aspartate aminotransferase (AST) activity in liver of a subject. In some embodiments, the magnitude of reduction of AST is at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%. In some embodiments, the magnitude of reduction of AST is from about 15% to about 80%, from about 25% to about 70%, or from about 30% to about 60%. In some embodiments, a reduction of AST results from a method of treating a disease or condition selected from alcoholic hepatitis, hepatic fibrosis, non-alcoholic fatty liver disease, non-alcoholic steatohepatitis, chronic kidney disease, a pulmonary fibrotic disorder, systemic scleroderma, or primary biliary cirrhosis. In some embodiments, the subject is a human. In some embodiments, the method further comprises administering to the subject one or more additional therapies. In some embodiments, the one or more therapies comprises effective amounts of prednisolone, pentoxifylline, or a diet and exercise regimen. In some embodiments, the subject is human and does not have type 2 diabetes.

In some embodiments, the methods of treatment result in a reduction of the fibrosis marker hepatic hydroxyproline. In some embodiments, the magnitude of reduction of hepatic hydroxyproline is at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%. In some embodiments, the magnitude of reduction of hepatic hydroxyproline is from about 15% to about 80%, from about 15% to about 60%, or from about 15% to about 35%. In some embodiments, a reduction of hydroxyproline results from a method of treating a disease or condition selected from alcoholic hepatitis, hepatic fibrosis, non-alcoholic fatty liver disease, non-alcoholic steatohepatitis, chronic kidney disease, a pulmonary fibrotic disorder, systemic scleroderma, or primary biliary cirrhosis. In some embodiments, the subject is a human. In some embodiments, the method further comprises administering to the subject one or more additional therapies. In some embodiments, the one or more therapies comprises effective amounts of prednisolone, pentoxifylline, or a diet and exercise regimen. In some embodiments, the subject is human and does not have type 2 diabetes.

In some embodiments, the methods of treatment result in a reduction in the marker bilirubin. In some embodiments, the magnitude of reduction of bilirubin is at least about 10%, at least about 20%, at least about 25%, at least about 30%, at least about 35%, at least about 40%, at least about 45%, or at least about 50%. In some embodiments, the magnitude of reduction of bilirubin is from about 10% to about 50%, from about 10% to about 35%, or from about 10% to about 25%. In some embodiments, a reduction of bilirubin results from a method of treating a disease or condition selected from alcoholic hepatitis, hepatic fibrosis, non-alcoholic fatty liver disease, non-alcoholic steatohepatitis, chronic kidney disease, a pulmonary fibrotic disorder, systemic scleroderma, or primary biliary cirrhosis. In some embodiments, the subject is a human. In some embodiments, the method further comprises administering to the subject one or more additional therapies. In some embodiments, the one or more therapies comprises effective amounts of prednisolone, pentoxifylline, or a diet and exercise regimen. In some embodiments, the subject is human and does not have type 2 diabetes.

In some embodiments, the methods of treatment result in a reduction of the fibrosis marker TGFβ1. In some embodiments, the magnitude of reduction of plasma TGFβ1 is at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%. In some embodiments, the magnitude of reduction of plasma TGFβ1 is from about 15% to about 80%, from about 15% to about 60%, or from about 15% to about 35%. In some embodiments, a reduction of TGFβ1 results from a method of treating a disease or condition selected from alcoholic hepatitis, hepatic fibrosis, non-alcoholic fatty liver disease, non-alcoholic steatohepatitis, chronic kidney disease, a pulmonary fibrotic disorder, systemic scleroderma, or primary biliary cirrhosis. In some embodiments, the subject is a human. In some embodiments, the method further comprises administering to the subject one or more additional therapies. In some embodiments, the one or more therapies comprises effective amounts of prednisolone, pentoxifylline, or a diet and exercise regimen. In some embodiments, the subject is human and does not have type 2 diabetes.

In some embodiments, the methods of treatment result in a reduction of plasma TNF-α. In some embodiments, the magnitude of reduction of plasma TNF-α is at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%. In some embodiments, the magnitude of reduction of plasma TNF-α is from about 15% to about 80%, from about 15% to about 60%, or from about 15% to about 35%. In some embodiments, a reduction of TNF-α results from a method of treating a disease or condition selected from alcoholic hepatitis, hepatic fibrosis, non-alcoholic fatty liver disease, non-alcoholic steatohepatitis, chronic kidney disease, a pulmonary fibrotic disorder, systemic scleroderma, or primary biliary cirrhosis. In some embodiments, the subject is a human. In some embodiments, the method further comprises administering to the subject one or more additional therapies. In some embodiments, the one or more therapies comprises effective amounts of prednisolone, pentoxifylline, or a diet and exercise regimen. In some embodiments, the subject is human and does not have type 2 diabetes.

In some embodiments, the methods of treatment result in a reduction of liver triglycerides. In some embodiments, the magnitude of reduction of liver triglycerides is at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%. In some embodiments, the magnitude of reduction of liver triglycerides is from about 15% to about 80%, from about 15% to about 60%, or from about 15% to about 35%. In some embodiments, a reduction of liver triglycerides results from a method of treating a disease or condition selected from alcoholic hepatitis, hepatic fibrosis, non-alcoholic fatty liver disease, non-alcoholic steatohepatitis, chronic kidney disease, a pulmonary fibrotic disorder, systemic scleroderma, or primary biliary cirrhosis. In some embodiments, the subject is a human. In some embodiments, the method further comprises administering to the subject one or more additional therapies. In some embodiments, the one or more therapies comprises effective amounts of prednisolone, pentoxifylline, or a diet and exercise regimen. In some embodiments, the subject is human and does not have type 2 diabetes.

In some embodiments, the methods of treatment result in an increase in plasma adiponectin. In some embodiments, the magnitude of increase in plasma adiponectin is at least about 30%, at least about 50%, at least about 75%, at least about 100%, at least about 125%, at least about 150%, at least about 200%, at least about 250%, at least about 300%, at least about 350%, at least about 400%, at least about 450%, or at least about 500%. In some embodiments, the magnitude of increase in plasma adiponectin is from about 30% to about 500%, from about 30% to about 250% or from about 30% to about 150%. In some embodiments, an increase in plasma adiponectin results from a method of treating a disease or condition selected from alcoholic hepatitis, hepatic fibrosis, non-alcoholic fatty liver disease, non-alcoholic steatohepatitis, chronic kidney disease, a pulmonary fibrotic disorder, systemic scleroderma, or primary biliary cirrhosis. In some embodiments, the subject is a human. In some embodiments, the method further comprises administering to the subject one or more additional therapies. In some embodiments, the one or more therapies comprises effective amounts of prednisolone, pentoxifylline, or a diet and exercise regimen. In some embodiments, the subject is human and does not have type 2 diabetes.

The methods of treatment of the present invention can be further defined based on the patient or subject who receives the treatment. In preferred embodiments, the subject is a human.

In some embodiments, the subject has diabetes. In some embodiments, the subject has type 2 diabetes. In some embodiments, the subject does not have diabetes. In some embodiments, the subject does not have type 2 diabetes.

In some embodiments, subject has a BMI of greater than 30. In some embodiments, the human subject has a BMI greater than 35. In some embodiments, the subject has a BMI greater than 40.

In some embodiments, the subject can also be defined based on having fibrosis, and the grade of fibrosis that the subject has. This, in some embodiments, the subject has an F1 grade of fibrosis (portal fibrosis without septa). In some embodiments the subject has an F2 grade of fibrosis (portal fibrosis with few septa). In some embodiments the subject has an F3 grade of fibrosis (numerous septa without cirrhosis).

In some embodiments, the subject can also be defined based on liver function. Thus, in some embodiments, the subject has an AST level less than the upper limit of normal, where normal ranges from 100 to 200 IU/L. In some embodiments, the subject has an AST level greater than the upper limit of normal. In some embodiments, the subject has an AST level more than two times greater than the upper limit of normal.

In some embodiments, the liver function can also be based on a measure of ALT, where the upper limit of normal is defined as 40 IU/L. Thus, in some embodiments, the subject has an ALT level less than the upper limit of normal. In some embodiments, the subject has an ALT level greater than the upper limit of normal. In some embodiments, the subject has an ALT level more than two times greater than the upper limit of normal.

In some embodiments, the liver function can also be based on a measure of alkaline phosphatase (ALP), where normal ranges from 44 to 147 IU/L. In some embodiments, the subject has an ALP level less than the upper limit of normal. In some embodiments, the subject has an ALP level greater than the upper limit of normal. In some embodiments, the subject has an ALP level more than two times greater than the upper limit of normal.

In some embodiments, a therapeutically effective amount of indeglitazar or a pharmaceutically acceptable salt thereof can be administered to the subject once, such as by a single injection, oral administration, or deposition at or near the site of interest. In some embodiments, a therapeutically effective amount of indeglitazar or a pharmaceutically acceptable salt thereof is administered to a subject daily over a period of days, weeks, months or even years. In some embodiments, a therapeutically effective amount of indeglitazar or a pharmaceutically acceptable salt thereof is administered at least once a day to a subject. Where a dosage regimen comprises multiple administrations, it is understood that the effective amount of the compound(s) or composition(s) administered to the subject can comprise the total amount of the compound(s) or composition(s) administered over the entire dosage regimen.

The dose of indeglitazar or a pharmaceutically acceptable salt thereof administered is not particularly limiting, provided the dose is sufficient to treat the disease or condition. The actual dosage amount of a composition of the present invention administered to a subject can be determined by physical and physiological factors such as body weight, severity of condition, the type of disease being treated, previous or concurrent therapeutic and/or prophylactic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In some embodiments, pharmaceutical compositions may comprise, for example, at least about 0.1% by weight of indeglitazar or a pharmaceutically acceptable salt thereof. In other embodiments, indeglitazar or a pharmaceutically acceptable salt thereof may comprise between about 2% to about 75% of the weight of the unit, or between about 10% to about 35% by weight, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, an effective amount of indeglitazar that is administered includes a dose of about 0.1 mg/kg body weight of the subject to about 20 mg/kg body weight of the subject. In some embodiments, an effective amount of indeglitazar that is administered includes a dose of about 0.5 mg/kg body weight of the subject to about 20 mg/kg body weight of the subject. In some embodiments, an effective amount of indeglitazar administered is from about 0.5 mg/kg to about 10 mg/kg. In some embodiments, an effective amount of indeglitazar administered is from about 0.5 mg/kg to about 3 mg/kg. Of course, all of these amounts are exemplary, and any amount in-between these points is also expected to be of use in the invention.

In some embodiments, the therapeutically effective amount in humans can range from about 15 mg/day to about 225 mg/day, from about 20 mg/day to about 225 mg/day, from about 30 mg/day to about 225 mg/day, or from about 60 mg/day to about 120 mg/day. In some embodiments, the therapeutically effective amount in humans comprises about 15 mg/day, about 20 mg/day, about 25 mg/day, about 30 mg/day, about 50 mg/day, about 60 mg/day, about 75 mg/day, about 100 mg/day, about 120 mg/day, about 150 mg/day, about 175 mg/day, about 200 mg/day or about 225 mg/day. In some embodiments, indeglitazar or a pharmaceutically acceptable salt thereof is administered orally to the subject.

When referring to dosages and doses, the dosage or dose is calculated on the weight of the indeglitazar. In some embodiments, indeglitazar may be administered as a pharmaceutically acceptable salt. Where indeglitazar is administered as a salt, the dose is still calculated on the basis of indeglitazar. For example a reference to a dose of 80 mg of indeglitazar salt means the dose of indeglitazar salt that is equivalent to 80 mg of indeglitazar.

In some embodiments, the methods of the present invention can further be defined based on the clinical characteristics of the patient or the clinical outcomes from the treatment. Thus, in any of the embodiments of the present invention:

the method occurs without causing edema in the human subject;

the method occurs without suppressing leptin concentrations in the human subject;

the method further comprises treating a fibrotic condition in the human subject by administering to the human subject the therapeutically effective amount of indeglitazar or a pharmaceutically acceptable salt thereof, wherein the fibrotic condition is preferably selected from the group consisting of liver fibrosis, fatty liver disease, non-alcoholic steatohepatitis, chronic kidney disease, a pulmonary fibrotic disorder, systemic scleroderma, acute alcoholic hepatitis, and primary biliary cirrhosis;

the method further comprises treating liver fibrosis in the human subject by administering to the human subject the therapeutically effective amount of indeglitazar or a pharmaceutically acceptable salt thereof, wherein the treatment of fibrosis preferably corresponds to an improvement in a fibrosis marker selected from hydroxyproline, TGF-β1, TIMP-1, TIMP-2, Hyaluronic acid, P3NP, NFS, FIB-4 score, ELF score, Pro-C3, and combinations thereof;

the method further comprises treating liver inflammation in the human subject by administering the therapeutically effective amount of indeglitazar or a pharmaceutically acceptable salt thereof, wherein the treatment of liver inflammation preferably corresponds to an improvement in fibrinogen, hsCRP, alpha2 macroglobulin, haptoglobin, or a combination thereof;

the method further comprises improving glucose metabolism in the human subject by comprising administering to the human subject the therapeutically effective amount of indeglitazar or a pharmaceutically acceptable salt thereof, wherein the improvement of glucose metabolism preferably corresponds to an improvement in fasting glucose, insulin, HOMA index, HbA1c, or a combination thereof;

the method further comprises treating liver steatosis in the human subject by administering to the human subject the therapeutically effective amount of indeglitazar or a pharmaceutically acceptable salt thereof;

the method further comprises treating hepatocyte ballooning in the human subject by administering to the human subject the therapeutically effective amount of indeglitazar or a pharmaceutically acceptable salt thereof;

the method further comprises increasing adiponectin in the human subject by administering to the human subject a therapeutically effective amount of indeglitazar or a pharmaceutically acceptable salt thereof;

the method further comprises improving liver enzyme function selected from AST, ALT, and ALP in the human subject by administering to the human subject the therapeutically effective amount of indeglitazar or a pharmaceutically acceptable salt thereof; and the method further comprises inducing weight loss in the human subject having a fibrotic condition by administering to the human subject the therapeutically effective amount of indeglitazar or a pharmaceutically acceptable salt thereof.

A pharmaceutical composition comprising indeglitazar can be in a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The disclosure further provides for a pharmaceutical composition comprising indeglitazar that can be administered in a convenient manner, such as by injection (subcutaneous, intravenous, etc.), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. In all cases, the composition should be sterile and should be fluid to the extent that easy syringability exists. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be typical to include isotonic agents, for example, sugars, poly-alcohols, such as mannitol, sorbitol, or sodium chloride in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the individual's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic/biocompatible in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions. The pharmaceutical composition can also be in the form of a polymorph, which might have more desirable crystal structure characteristics compared to the original molecular entity.

Sample Embodiments

This section describes exemplary compositions and methods of the invention, presented without limitation, as a series of claims, some or all of which may be alphanumerically designated for clarity and efficiency. Each of these paragraphs can be combined with one or more other paragraphs, and/or with disclosure from elsewhere in this application, including the materials incorporated by reference, in any suitable manner. Some of the paragraphs below expressly refer to and further limit other paragraphs, providing without limitation examples of some of the suitable combinations.

1. A method of treating a fibrotic liver disease or condition in a human subject, comprising administering to the subject a therapeutically effective amount of indeglitazar or a pharmaceutically acceptable salt thereof.
2. A method of treating alcoholic hepatitis in a human subject, comprising administering to the subject a therapeutically effective amount of indeglitazar or a pharmaceutically acceptable salt thereof.
3. A method of treating fatty liver disease (liver steatosis) in a human subject, comprising administering to the subject a therapeutically effective amount of indeglitazar or a pharmaceutically acceptable salt thereof.
4. A method of treating non-alcoholic fatty liver disease in a human subject, comprising administering to the subject a therapeutically effective amount of indeglitazar or a pharmaceutically acceptable salt thereof.
5. A method of treating non-alcoholic steatohepatitis in a human subject, comprising administering to the subject a therapeutically effective amount of indeglitazar or a pharmaceutically acceptable salt thereof.
6. A method of treating liver fibrosis in a human subject, comprising administering to the subject a therapeutically effective amount of indeglitazar or a pharmaceutically acceptable salt thereof.
7. The method of any of paragraphs 1-6, wherein the treatment results in an improvement in a fibrosis marker selected from TIMP-1, TIMP-2, hyaluronic acid, P3NP, NFS, FIB-4 score, ELF score, Pro-C3, and combinations thereof.
8. The method of any of paragraphs 1-7, wherein the treatment results in a reduction of alanine aminotransferase (ALT) activity in liver of the subject.
9. The method of paragraph 8, wherein the magnitude of reduction of ALT is at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%.
10. The method of any of paragraphs 1-9, wherein the treatment results in a reduction of the fibrosis marker hepatic hydroxyproline.
11. The method of paragraph 10, wherein the magnitude of reduction of hepatic hydroxyproline is at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%.
12. The method of any of paragraphs 1-11, wherein the treatment results in a reduction in the marker bilirubin.
13. The method of paragraph 12, wherein the magnitude of reduction of bilirubin is at least about 10%, at least about 20%, at least about 25%, at least about 30%, at least about 35%, at least about 40%, at least about 45%, or at least about 50%.
14. The method of any of paragraphs 1-13, wherein the treatment results in a reduction in plasma TGFβ1.
15. The method of paragraph 14, wherein the magnitude of reduction of plasma TGFβ1 is at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%.
16. The method of any of paragraphs 1-15, wherein the treatment results in a reduction in plasma TNF-α.
17. The method of paragraph 16, wherein the magnitude of reduction of plasma TNF-α is at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%.
18. The method of any of paragraphs 1-17, wherein the treatment results in a reduction of liver triglycerides.
19. The method of paragraph 18, wherein the magnitude of reduction of liver triglycerides is at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%,
20. The method of any of paragraphs 1-19, wherein the treatment results in an increase in plasma adiponectin.
21. The method of paragraph 20, wherein the magnitude of increase in plasma adiponectin is at least about 30%, at least about 50%, at least about 75%, at least about 100%, at least about 125%, at least about 150%, at least about 200%, at least about 250%, at least about 300%, at least about 350%, at least about 400%, at least about 450%, or at least about 500%.
22. The method of any of paragraphs 1-21, wherein the treatment results in a reduction of alanine aminotransferase (AST) activity in liver of the subject.
23. The method of paragraph 22, wherein the magnitude of reduction of AST is at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%.
24. The method of any of the paragraphs 1-23, wherein the subject has type 2 diabetes.
25. The method of any of the paragraphs 1-23, wherein the subject does not have type 2 diabetes.
26. The method of any of paragraphs 1-25, wherein hepatocellular karyomegaly is reduced.
27. The method of any of paragraphs 1-26, wherein hepatocyte ballooning is reduced.
28. The method of any of paragraphs 2 and 7-27, wherein the treatment of alcoholic hepatitis results in an improvement in levels of fibrinogen, hsCRP, alpha2 macroglobulin, haptoglobin, or a combination thereof.
29. The method of any of any of paragraphs 1-28, wherein the subject has a BMI greater than 30.
30. The method of any of paragraphs 1-28, wherein the subject has a BMI greater than 35.

31. The method of any of paragraphs 1-28, wherein the subject has a BMI greater than 40.
32. The method of any of paragraphs 1-31, wherein the subject has an F1 grade of fibrosis.
33. The method of any of paragraphs 1-31, wherein the subject has an F2 grade of fibrosis.
34. The method of any of paragraphs 1-31, wherein the subject has an F3 grade of fibrosis.
35. The method of any of paragraphs 1-34, wherein the subject has an AST level less than the upper limit of normal.
36. The method of any of paragraphs 1-34, wherein the subject has an AST level greater than the upper limit of normal.
37. The method of any of paragraphs 1-34, wherein the subject has an AST level more than two times greater than the upper limit of normal.
38. The method of any of paragraphs 1-37, wherein the subject has an ALT level less than the upper limit of normal.
39. The method of any of paragraphs 1-37, wherein the subject has an ALT level greater than the upper limit of normal.
40. The method of any of paragraphs 1-37, wherein the subject has an ALT level more than two times greater than the upper limit of normal.
41. The method of any of paragraphs 1-40, wherein the subject has an ALP level less than the upper limit of normal.
42. The method of any of paragraphs 1-40, wherein the subject has an ALP level greater than the upper limit of normal.
43. The method of any of paragraphs 1-40, wherein the subject has an ALP level more than two times greater than the upper limit of normal.
44. The method of any of paragraphs 1-43, wherein the therapeutically effective amount of indeglitazar comprises from about 20 mg/day to about 120 mg/day.
45. The method of any of paragraphs 1-43, wherein the therapeutically effective amount of indeglitazar comprises from about 20 mg/day to about 80 mg/day.
46. The method of any of paragraphs 1-43, wherein the therapeutically effective amount of indeglitazar comprises about 30 mg/day or about 60 mg/day.
47. The method of any of paragraphs 1-43, wherein the therapeutically effective amount of indeglitazar comprises from about 40 mg/day to about 120 mg/day.
48. The method of any of paragraphs 1-43, wherein the therapeutically effective amount of indeglitazar comprises about 50 mg/day or about 100 mg/day.
49. The method of any of paragraphs 1-48, wherein indeglitazar is administered orally.
50. The method of any of paragraphs 1-49, wherein the method occurs without causing edema in the subject.
51. The of any of paragraphs 1-50, wherein the method occurs without suppressing leptin concentrations in the subject.
52. The method of any of paragraphs 1-51, wherein the method further treats liver inflammation in the subject.
53. The method of paragraph 52, wherein the treatment of liver inflammation corresponds to an improvement in fibrinogen, hsCRP, alpha2 macroglobulin, haptoglobin, or a combination thereof.
54. The method of any of paragraphs 1-53, wherein the method improves glucose metabolism in the subject.
55. The method of paragraph 54, wherein the improvement of glucose metabolism corresponds to an improvement in fasting glucose, insulin, HOMA index, HbA1c, or a combination thereof.
56. The method of any of paragraphs 1-55, further comprising administering one or more additional therapies.
57. The method of paragraph 56, wherein the one or more additional therapies comprises a therapeutically active agent.
58. The method of paragraph 57, wherein the therapeutically active agent comprises an effective amount of prednisolone.
59. The method of any of paragraphs 56-58, wherein the therapeutically active agent is for promoting weight loss.
60. The method of paragraph 59, wherein the therapeutically active agent is a GLP-1 agonist.
61. The method of any of paragraphs 56-60, wherein the one or more additional therapies comprises exercise, a modification to the subject's diet or both.
62. The method of any of paragraphs 1-61, wherein the method results in an improvement by one or more grades in the NAS (NAFLD Activity Score).
63. The method of any of paragraphs 1-62, wherein the method results in an improvement in NASH CRN fibrosis score.
64. The method of any of paragraphs 1-63, further comprising administering an effective amount of resmetirom to the subject.

All publications herein are incorporated by reference to the same extent as if each individual publication or patent application was specifically and individually indicated to be incorporated by reference.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLES

Example 1. Evaluation of Indeglitazar in a Mouse Model of Human Alcoholic Hepatitis In this example, the efficacy of 3 daily doses (10, 30, and 50 mg/kg) of indeglitazar in a mouse (male and female mice) model of human alcoholic hepatitis was evaluated. The objective is to identify the most effective dose(s) of indeglitazar on a battery of validated markers, using a previously described mouse model of AH.

Materials and Methods

Mouse model generation and treatment. The AH mouse model was generated as described in Shah et al. through chronic and binge ethanol feeding plus lipopolysaccharides (LPS) administration to provide a second hit to increase liver damage (Shah R et al., Oxid Med Cell Longev, (2018), 2018:9630175; Lamas-Paz A et al., World J Gastroenterol, (2018), 24:5063-75). This model is easy to implement and recapitulates the major features of human AH including marked ALT elevation, liver steatosis, and fibrosis (O'Beirne J., Dig Dis Sci., (2020), 65:920-1). A total of 60 mice, were used at a 50:50 male/female ratio to provide a comprehensive representation applicable in treating the general population. C57BL6 mice (6-8-week-old) were fed Lieber-DeCarli '82 rodent liquid diet (LDC) ad libitum for 5 days to acclimatize them to tube feeding. On day 6, mice were treated according to Table 1. Ethanol-fed groups were allowed free access to LDC diet containing 5% (vol/vol) ethanol for 11 days, and control groups were pair-fed with the LDC diet only. Indeglitazar was administered by oral gavage starting from day 6. On day 12, mice were given a single dose of 5 g/kg/bw of EtOH by oral gavage, and LPS (2 mg/kg/bw) by intraperitoneal injection (IP), pair-fed mice were fed isocaloric maltose dextrin and all mice were euthanized 6 h later. LDC diet consumption was monitored daily to ensure that indeglitazar did not affect food intake.

TABLE 1

Study Groups

| Group # | Mice (M/F) | Indeglitazar (mg/kg) | Protocol (Day 6-12) | Alcohol Binge Plus LPS (IP) |
|---|---|---|---|---|
| 1 | 6/6 | 10 | LCD diet with ethanol plus indeglitazar by oral gavage | Day 12 |
| 2 | 6/6 | 30 | LCD diet with ethanol plus indeglitazar by oral gavage | Day 12 |
| 3 | 6/6 | 50 | LCD diet with ethanol plus indeglitazar by oral gavage | Day 12 |
| 4 | 6/6 | Vehicle | LCD diet with ethanol plus vehicle | Day 12 |
| 5 | 6/6 | Vehicle | LCD diet without ethanol plus vehicle | None |

Table 1 Study groups. Indeglitazar dosing selected on the basis of previous experiments conducted in a mouse model of NASH Analysis and tests: Mice were treated for 11 days; body weights were measured before and during administration. Plasma was analyzed for ALT, AST, and GGT. A full necropsy was performed at the end-point together with liver histology to assess steatosis, and inflammatory infiltrates. Briefly, liver tissue was fixed in 10% neutral buffered formalin and paraffin-embedded, sectioned into 5 am thickness, and stained with hematoxylin-eosin (H&E) and Oil-Red 0 staining for evaluation of histopathological changes. Stained liver slices were analyzed under a bright-field microscope using the histological scoring system for non-alcoholic fatty liver disease (Kleiner D L et al., Hepatology, (2005), 41:1313-21). The remaining liver tissue was analyzed for liver triglycerides and cholesterol levels by biochemical assays.

Results

Figure 6:
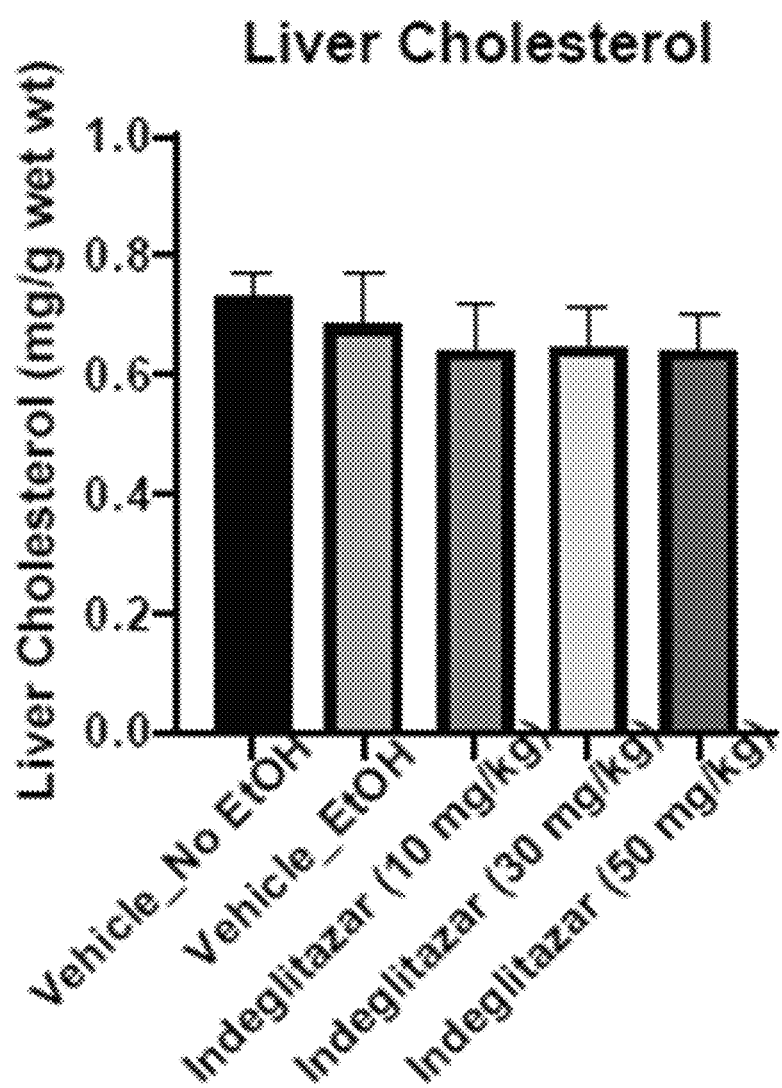
FIG. 6. Indeglitazar (10, 30, 50 mg/kg/day) had no significant effect on liver total cholesterol in the ethanol-treated mouse (male and female mice) model of human AH described in Example 1.
Figure 7:
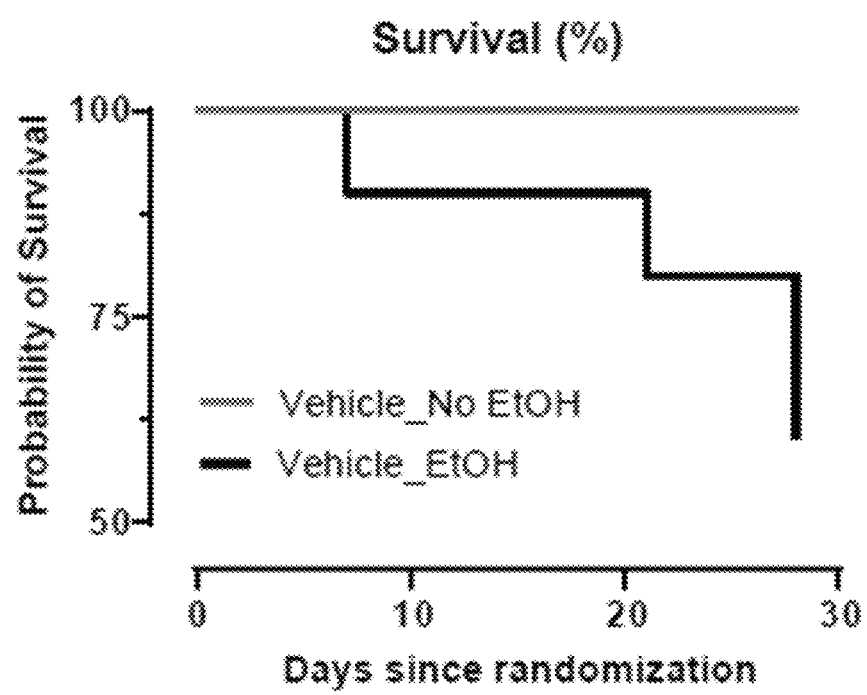
FIG. 7. Ethanol vehicle significantly decreased overall survival in the ethanol-treated mouse (male and female mice) model of human AH described in Example 2.
Figure 8:
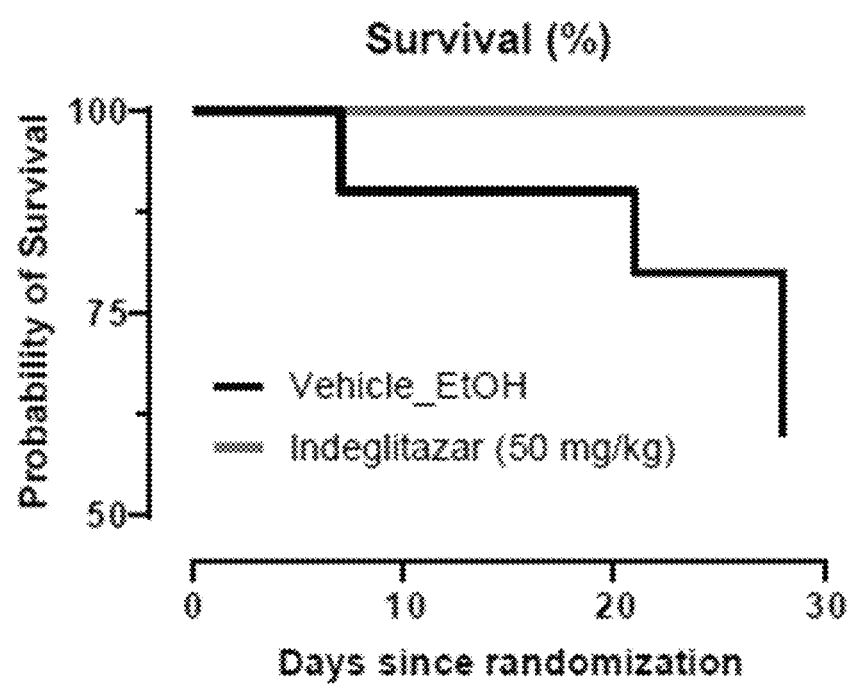
FIG. 8. Indeglitazar (50 mg/kg/day) significantly increased overall survival in the ethanol-treated mouse (male and female mice) model of human AH described in Example 2.
Figure 14:
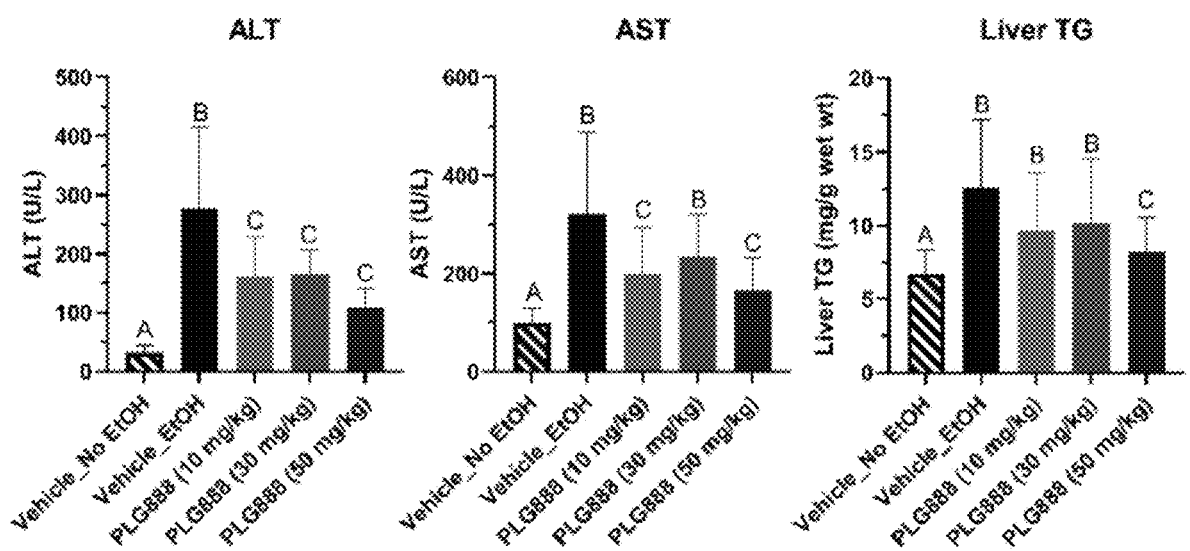
FIG. 14. Effects of indeglitazar on alanine aminotransferase (ALT), aspartate aminotransferase (AST), hepatic triglycerides (TG) in the NIAAA mouse model. Different letters represent statistically significant values from appropriate vehicle; $P<0.05$ or lower.

Results are depicted in FIGS. 1, 6, and 14 and summarized as follows: the efficacy of 3 daily doses (10, 30, and 50 mg/kg) of orally administered (by gavage) indeglitazar in a mouse (male and female mice) model of human alcoholic hepatitis was evaluated. Indeglitazar had no significant effect on body weight compared to the ethanol-treated vehicle control, at any dose evaluated (FIG. 1). In vehicle-treated mice, ethanol treatment caused a significant increase in the enzyme ALT (FIG. 14). All three doses of indeglitazar caused a significant decrease in ALT compared to the ethanol-treated vehicle control group. In vehicle-treated mice, ethanol treatment caused a significant increase in the enzyme AST (FIG. 14). Indeglitazar (10 and 50 mg/kg) caused a significant decrease in AST compared to the ethanol-treated vehicle control group. Indeglitazar also reduced liver triglycerides (50 mg/kg), a marker of hepatic steatosis (FIG. 14), but had no significant effect on liver total cholesterol (FIG. 6).

Conclusion

Indeglitazar produced significant beneficial effects on two validated markers of liver function, ALT and AST, without causing a significant effect on body weight. Based on this dose response study, the 50 mg/kg daily dose of indeglitazar was selected for further evaluation in Example 2.

Example 2. In Vivo Efficacy and Safety Evaluation of Indeglitazar in a Mouse Model of Human Alcoholic Hepatitis The objective of this example is to examine the efficacy and safety of indeglitazar in reducing the detrimental effects of ethanol, a preclinical study was conducted using the previously described mouse model of AH. Indeglitazar was evaluated at the best dose identified in Example 1, and in combination with standard clinical therapy: prednisolone.

Mouse model generation and treatment. Mice were generated as described in Example 1. Mice were fed with the ethanol diet for four weeks, followed by 4 weeks of intervention (8 weeks total treatment). Groups and treatment are shown in Table 2. At endpoint, groups 1-4 were gavaged, in the early morning, with a single dose of ethanol plus LPS by IP injection as in Example 1 and group 5 with isocaloric maltose dextrin and euthanized 6 h later.

TABLE 2

Study Groups

| Group # | Mice (M/F) | Indeglitazar (mg/kg) | Protocol (Day 6-12) |
|---|---|---|---|
| 1 | 10/10 | 50 | LCD diet with ethanol plus indeglitazar by oral gavage |
| 2 | 10/10 | None | LCD diet with ethanol plus prednisolone (10 mg/kg) by oral gavage |
| 3 | 10/10 | 50 | LCD diet with ethanol plus indeglitazar + prednisolone (10 mg/kg) by oral gavage |
| 4 | 10/10 | Vehicle | LCD diet with ethanol plus vehicle |
| 5 | 10/10 | Vehicle | LCD diet without ethanol plus vehicle |

Table 2 Study groups. Indeglitazar dosing selected on the basis of dose response experiment (Example 2).

Efficacy in reducing Liver damage: The ability to reduce key markers of liver damage were assessed by evaluation of ALT, AST, and GGT levels at day 28 (4 weeks) before starting indeglitazar administration and at the end-point (8 weeks). Livers were collected at the end-point from all mice and weighed. Liver samples were processed for histology to assess steatosis, inflammatory infiltrates and fibrosis. Briefly, liver tissue was fixed in 4% paraformaldehyde and paraffin-embedded, sectioned into 5 m thickness, and stained with hematoxylin-eosin (H&E), Oil-Red O staining, and Masson's trichrome staining. The histopathological changes of stained liver slices were observed under a bright-field microscope and scored according to Kleiner, D. E. et al (Kleiner D E et al., Hepatology, (2005), 41:1313-21).

Efficacy in reducing AH mediated inflammation: AH is characterized by non-resolving inflammation caused by DAMPs and PAMPs (Lucey M R et al., N Engl J Med, (2009), 360:2758-69; Saha B et al., Hepatology, (2019), 70:1134-49; Szabo G et al., Alcohol Alcohol, (2017), 52:414-24. To assess indeglitazar anti-inflammatory activity, plasma levels of CRP, adiponectin, and pro-inflammatory cytokines IL-6, IL-8, TNFα, IFNγ, TGF-β were evaluated by ELISA (Crews F T et al., Alcohol Clin Exp Res, (2006), 30:720-30).

Safety testing: The safety of indeglitazar treatment was assessed by body weight measurements and full necropsy at endpoint. Mice were terminated from the experiment by isoflurane anesthesia and blood was collected by a cardiac bleed into EDTA-treated tubes, and then centrifuged to obtain plasma to conduct clinical chemistry including full liver and renal toxicology panel. A portion of the liver was analyzed for liver triglycerides and cholesterol levels by biochemical assays. Possible indeglitazar extra hepatic actions was evaluated, specifically cardiac toxicity. Hearts were weighted and fixed in 10% NBF, paraffin embedded, and sectioned into 4-μm thick slices. H&E staining was used to investigate myocardial cell hypertrophy, and ventricle diameters by microscopy. Since myocardial lipid accumulation in response to PPAR-γ expression in the heart has been associated to cardiac hypertrophy and increased cardiomyocyte apoptosis, lipid accumulation and apoptosis was evaluated by Oil Red Staining and TUNEL assay (He L et al., Circulation, (2012), 126:1705-16; Son N H et al., J Clin Invest, (2007), 117:2791-801; Son N H et al., J Clin Invest, (2010), 120:3443-54).

Results Results (male and female mice, except where noted) are depicted in FIGS. 2, 3, 4, 5, 15 and 16 (male and female mice) and summarized as follows: the efficacy of indeglitazar was evaluated at a daily dose of 50 mg/kg, and this same dose was also evaluated in combination with the standard of care treatment for human AH, prednisolone (10 mg/kg, oral gavage).

Figure 2:
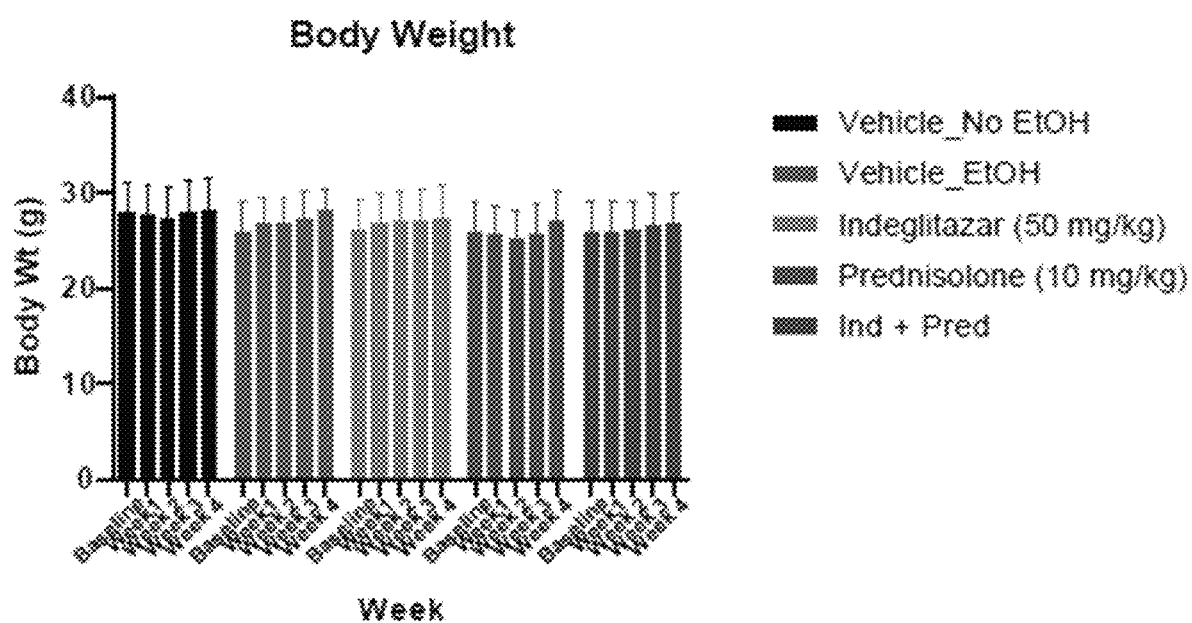
FIG. 2. Indeglitazar (50 mg/kg/day) has no significant effect on body weight in the ethanol-treated mouse (male and female mice) model of human AH described in Example 2.
Figure 3:
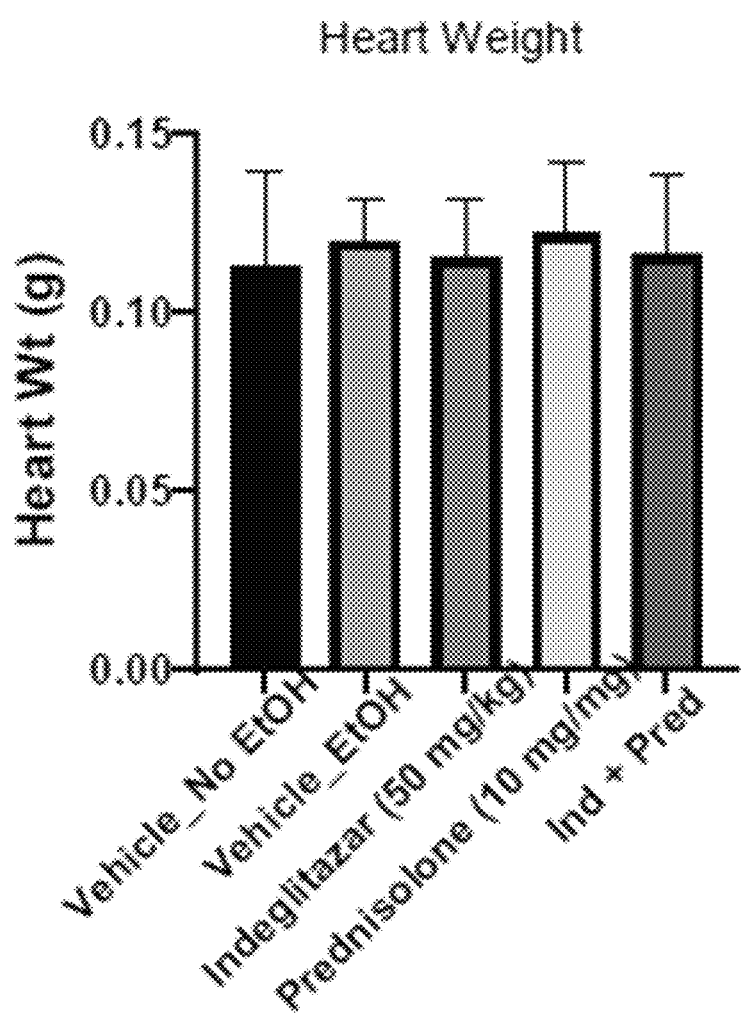
FIG. 3. Indeglitazar (50 mg/kg/day) has no significant effect on heart weight (actual) in the ethanol-treated mouse (male and female mice) model of human AH described in Example 2.
Figure 4:
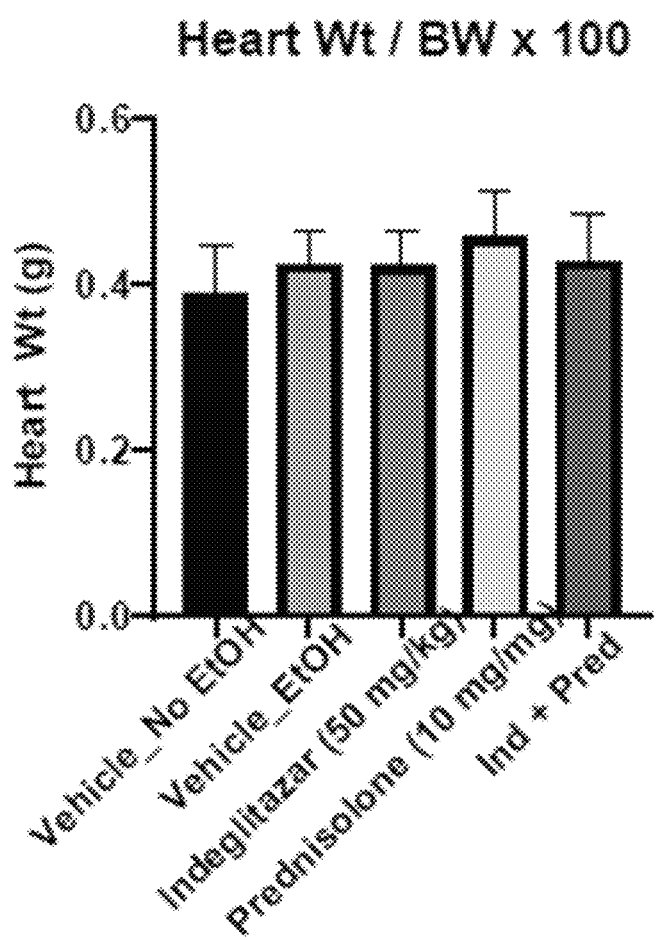
FIG. 4. Indeglitazar (50 mg/kg/day) has no significant effect on heart weight divided by body weight×100 in the ethanol-treated mouse (male and female mice) model of human AH described in Example 2.
Figure 5:
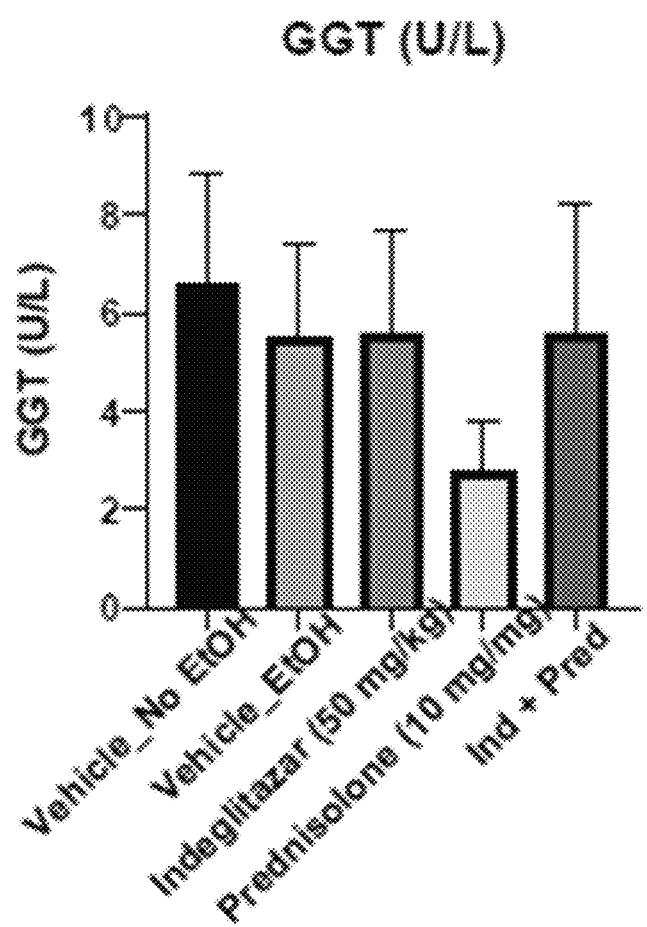
FIG. 5. Indeglitazar (50 mg/kg/day) has no significant effect on gamma-glutamyl transferase (GGT) in the ethanol-treated mouse (male and female mice) model of human AH described in Example 2.
Figure 9:
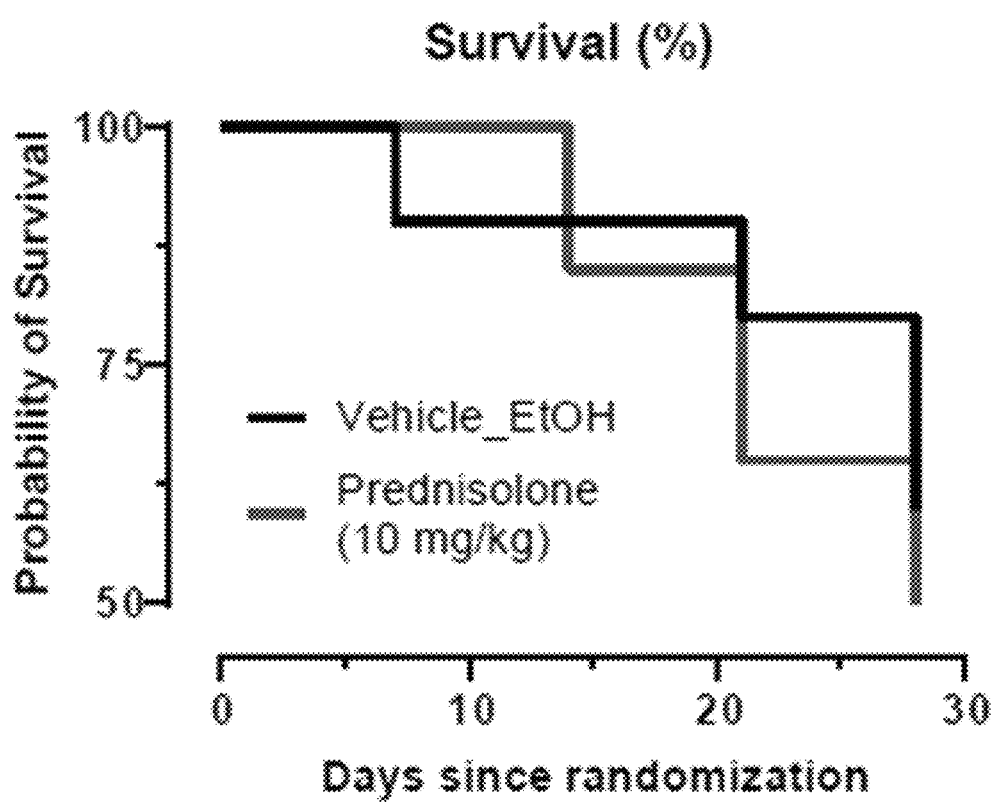
FIG. 9. Prednisolone (10 mg/kg/day) had no significant effect on survival in the ethanol-treated mouse (male and female mice) model of human AH described in Example 2.
Figure 10:
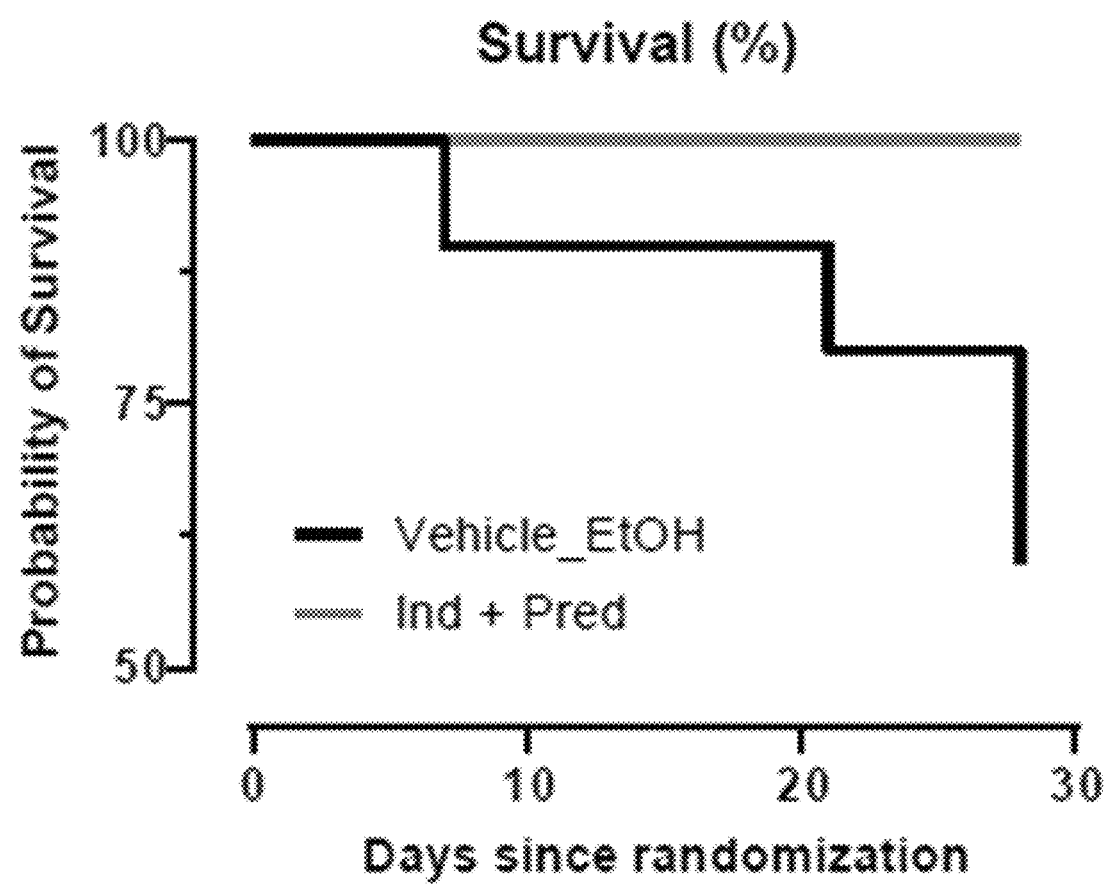
FIG. 10. The combination of indeglitazar (50 mg/kg/day and prednisolone (10 mg/kg/day) significantly increased overall survival in the ethanol-treated mouse (male and female mice) model of human AH described in Example 2.
Figure 15:
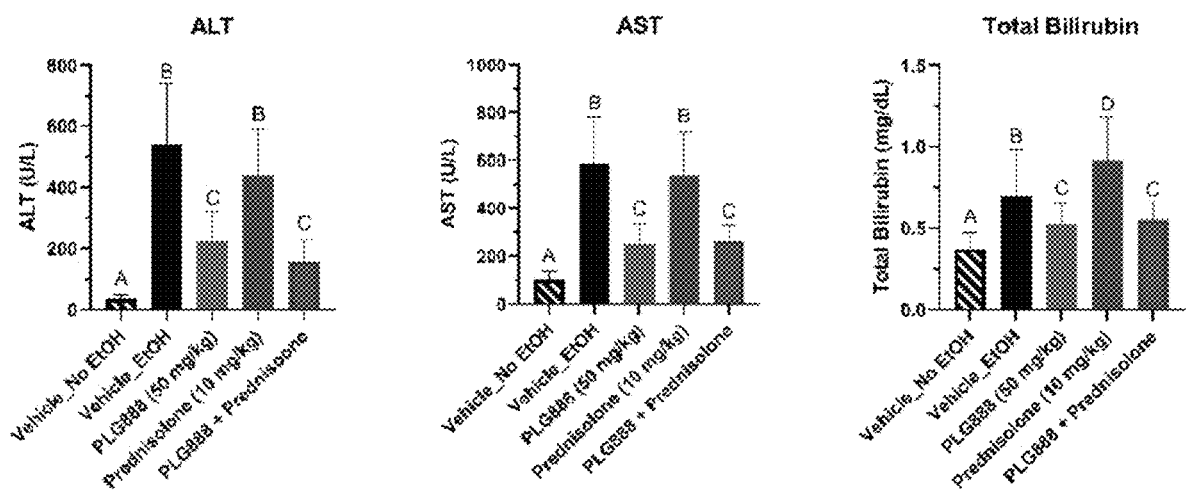
FIG. 15. Effects of indeglitazar on alanine aminotransferase (ALT), aspartate aminotransferase (AST), and total bilirubin in the NIAAA mouse model. Different letters represent statistically significant values from appropriate vehicle; $P<0.05$ or lower.
Figure 16:
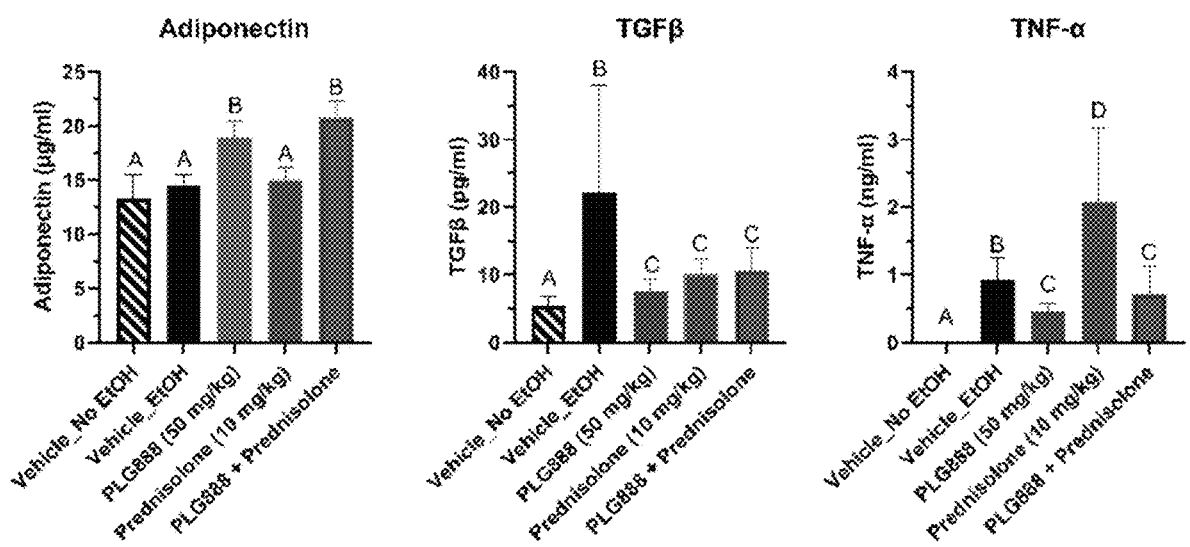
FIG. 16. Effects of indeglitazar on adiponectin, TGFβ1, and TNF-α in the NIAAA mouse model. Different letters represent statistically significant values from appropriate vehicle; $P<0.05$ or lower.
Figure 17:
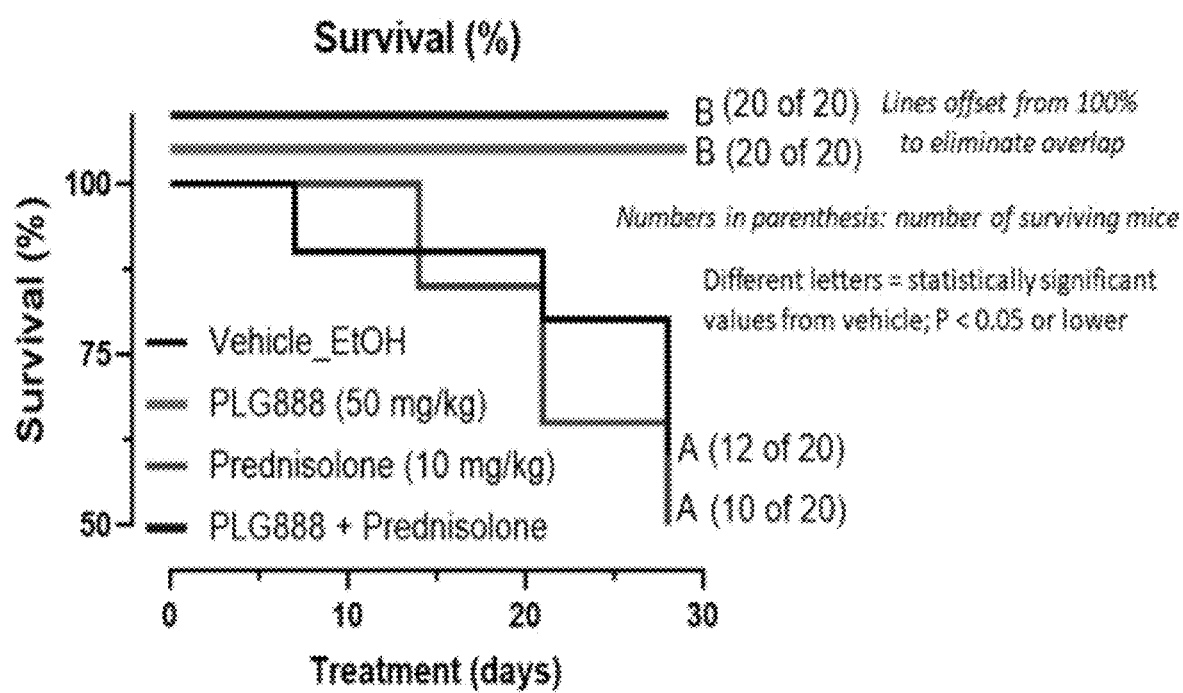
FIG. 17. Effect of indeglitazar on overall survival in the NIAAA mouse model. Different letters represent statistically significant values from appropriate vehicle; $P<0.05$ or lower.

- In vehicle-treated mice, ethanol treatment had no significant effect on body weight (FIG. 2). Indeglitazar had no significant effect on body weight compared to the ethanol-treated vehicle control, either alone or in combination with prednisolone (FIG. 2).
- In vehicle-treated mice, ethanol treatment had no significant effect on heart weight (FIGS. 3 and 4). Indeglitazar had no significant effect on heart weight (actual or expressed as a function of body weight) compared to the ethanol-treated vehicle control, either alone or in combination with prednisolone (FIGS. 3 and 4).
- In vehicle-treated mice, ethanol treatment caused a significant increase in the enzyme ALT (FIG. 15). Indeglitazar caused a significant decrease in ALT compared to the ethanol-treated vehicle control group, both alone and in combination with prednisolone (FIG. 15).
- In vehicle-treated mice, ethanol treatment caused a significant increase in the enzyme AST (FIG. 15). Indeglitazar caused a significant decrease in AST compared to the ethanol-treated vehicle control group, both alone and in combination with prednisolone (FIG. 15).
- In vehicle-treated mice, ethanol treatment had no effect on the enzyme GGT (FIG. 5). Indeglitazar had no effect on the enzyme GGT compared to the ethanol-treated vehicle control group, either alone or in combination with prednisolone (FIG. 5).
- In vehicle-treated mice, ethanol treatment caused a significant increase in total bilirubin (FIG. 15). Indeglitazar caused a decrease total bilirubin compared to the ethanol-treated vehicle control group. In combination with prednisolone, indeglitazar also caused a decrease total bilirubin compared to the ethanol-treated vehicle control group but the magnitude of effect did not reach statistical significance as judged by ANOVA and Dunnett's post-test (FIG. 15).
- In vehicle-treated mice (male and female), ethanol treatment caused a slight increase in plasma adiponectin (FIG. 16). Indeglitazar caused a significant increase in plasma adiponectin compared to the ethanol-treated vehicle control group, both alone and in combination with prednisolone (FIG. 16).
- In vehicle-treated mice (male and female), ethanol treatment caused a significant decrease in overall survival (FIGS. 7-10 and 17). Indeglitazar caused a significant increase in overall survival (FIGS. 8 and 17) compared to the ethanol-treated vehicle control group, both alone and in combination with prednisolone (FIGS. 10 and 17). Prednisolone had no significant effect on overall survival time (FIG. 9).

Conclusion

Indeglitazar produced significant beneficial effects on two validated markers of liver function, ALT and AST, without causing a significant effect on body weight, heart weight, or other important indices of safety. Indeglitazar also caused a significant increase in plasma adiponectin, which is an important adipokine that increases insulin sensitivity and facilitates fat-burning. Increased adiponectin is beneficial in AH, NAFLD, and NASH, since it is anti-fibrotic and facilitates fat-burning in the liver.

Example 3. Human Clinical Study Evaluating the Safety and Effectiveness of Indeglitazar in Human Alcoholic Hepatitis Based on the promising animal data reported in Examples 1 and 2, a clinical study has been designed to evaluate indeglitazar's ability to treat AH in humans, based on the following parameters as set forth in Table 3.

TABLE 3

| Phase 2A Clinical Study of Indeglitazar in Human Alcoholic Hepatitis. | |
|---|---|
| Protocol Synopsis: Phase 2A Proof of Concept | |
| Name of Active Ingredient(s) | INDEGLITAZAR (indeglitazar) |
| Title of Study | A Randomized, Open-Label, Dose Escalation Study to Assess the Safety and Pharmacodynamics (PD) of Indeglitazar in Patients with Alcoholic Hepatitis |
| Study Center(s) | Multi-center trial; approximately 5-15 centers (countries and locations TBD) |
| Phase of Development | Phase 2A |
| Objectives | Evaluation of the Safety and Pharmacodynamics of Indeglitazar (3 doses) on Parameters of Alcoholic Hepatitis (AH) |

TABLE 3-continued

Phase 2A Clinical Study of Indeglitazar in Human Alcoholic Hepatitis.

Protocol Synopsis: Phase 2A Proof of Concept

| | |
|---|---|
| Methodology | Screening: according to approved inclusion and exclusion criteria<br>Safety: as judged by standard of care and PI(s)<br>Randomization to 1 of 3 dosage groups will occur at the Baseline Visit (Day 0) and according to severity of AH<br>Assessments of all key evaluation parameters will occur during the Baseline Visit, Day 7, and at the End of Treatment Visit (Visit 2; Day 7; Day 28-30), Subjects will return 4 weeks following last dose of study material for an assessment of safety. |
| Number of Subjects | N = 48 (N = 24 Moderate AH (MELD = 11-20) and N = 24 Severe AH (MELD = 21-30) (N = 8 per dose) |
| Diagnosis and Main Criteria for Inclusion | 1. Able to provide written informed consent (either from patient or patient's legally acceptable representative)<br>2. Male or female patients 21 years of age to 75 years of age with BMI ≥20 to ≤45 kg/m²<br>3. Patients with alcoholic hepatitis defined as:<br>a. History of heavy alcohol abuse: >40 g/day in females or >60 g/day in males for a minimum period of 6 months, AND<br>b. Consumed alcohol within 12 weeks of entry into the study, AND<br>c. Serum bilirubin >3 mg/dL AND AST > ALT, but less than 300 U/L AND<br>d. Onset of jaundice within prior 8 weeks<br>e. AST/ALT > 1.5<br>f. MELD score between 11-30, inclusive<br>g. Maddrey's discriminant function ≥32<br>4. No evidence of active infection as determined by the investigator. If infection is initially suspected clinically,<br>a. blood cultures, urine cultures, and peritoneal cultures should be without growth for 48 h, AND<br>b. peritoneal cell count should be less than 250 Polymorphonuclear cell (PMN)/ml. If infection is diagnosed, then the infection must be<br>c. treated with antibiotics, AND<br>d. documented negative blood cultures for 48 h, or for spontaneous bacterial peritonitis (SBP) 25% reduction in PMN count prior to enrollment.<br>5. Women of child-bearing potential (defined as females who are not surgically sterile or who are not over the age of 52 and amenorrheic for at least 12 months) must utilize appropriate birth control throughout the study duration. Acceptable methods that may be used are abstinence, birth control pills ("The Pill") or patch, diaphragm, intrauterine device (IUD/coil), vaginal ring, condom, surgical sterilization or progestin implant or injection, or sexual activity limited to a sterile (e.g., vasectomized) male partner.<br>6. Male patients must agree to use a medically acceptable method of contraception/birth control throughout the study duration. |
| Main Criteria for Exclusion | 1. Other or concomitant cause(s) of liver disease as a result of:<br>a. Autoimmune liver disease (positive anti-mitochondrial antibody and smooth muscle antibody, positive reading on anti-nuclear antibody titer > 1:160)<br>b. Wilson disease (ceruloplasmin levels <10 mcg/L)<br>c. Vascular liver disease<br>d. Drug induced liver disease<br>e. Surface antigen positive hepatitis B (HBsAg+). Note: patients with isolated core antibody (HBcAb) are not excluded.<br>f. Acute hepatitis A<br>g. Acute HCV or chronic hepatitis C with a history of decompensated cirrhosis. Note: patients with stable chronic Hep C Virus (HCV) or successfully treated HCV are not excluded.<br>2. Co-infection with human immunodeficiency virus (HIV)<br>3. Positive Urine Drug Screen (amphetamines, barbiturates, benzodiazepines, cocaine and opiates) except THC and legal prescription medications. |

TABLE 3-continued

Phase 2A Clinical Study of Indeglitazar in Human Alcoholic Hepatitis.

Protocol Synopsis: Phase 2A Proof of Concept

|  |  |
|---|---|
|  | 4. Any active malignancies other than curatively treated skin cancer (basal cell or squamous cell carcinomas) or any other malignancy diagnosed within the last five years<br>5. Active tuberculosis on chest x-ray at study entry<br>6. Significant systemic or major illness other than liver disease, including coronary artery disease, cerebrovascular disease, pulmonary disease, renal failure, serious psychiatric disease, that, in the opinion of the Investigator would preclude the patient from participating in and completing the study<br>7. Patients requiring the use of vasopressors or inotropic support. Prior use of inotropic support will be allowed if the condition has stabilized within the first 7 days of admission to the hospital<br>8. Liver biopsy, if carried out, showing findings not compatible with AH<br>9. Any patient that has received any investigational drug or device within 30 days of dosing or who is scheduled to receive another investigational drug or device at any time during the study<br>10. Patients who are taking drug products that are primarily the substrates of CYP2C8, such as chloroquine, paclitaxel, rosiglitazone, repaglinide<br>11. Corticosteroid use ≥3 months<br>12. If female, known pregnancy, or has a positive serum pregnancy test, or is lactating/breastfeeding<br>13. Serum creatinine > 2.5 mg/dL<br>14. Patients who have had organ transplantation (such as liver, kidney, lung, heart, bone marrow, or stem cell etc.), other than cornea transplant<br>15. Stage 3 or greater encephalopathy by West Haven criteria<br>16. Pancreatitis, or active gastrointestinal bleeding<br>17. Positive COVID-19 infection (by PCR)<br>18. Active infection or sepsis |
| Randomization | Stratification of subjects: as recommended by expert biostatistician |
| Test Product, Dose, Mode of Administration | INDEGLITAZAR 30 mg p.o. QD (50 mg, if permitted by regulatory authority(s)<br>INDEGLITAZAR 60 mg p.o. QD (100 mg, if permitted by regulatory authority(s)<br>INDEGLITAZAR 120 mg p.o. QD (150 mg, if permitted by regulatory authority(s) |
| Reference Therapy, Dose, Mode of Administration | Not applicable |
| Duration of Treatment and Follow-Up | The intervention period for all randomized subjects will be 30 days (Final duration of intervention to be determined by consensus of expert advisors/CRO and financial considerations). Intervention period will be followed by a 30-day safety follow-up period, in which subjects will continue on their standard of care, but will not continue on the study drug. |
| Criteria for Evaluation | 1. Assessment of Treatment-Emergent Adverse Events. Time Frame: 4.5 years. Assess the safety and tolerability of INDEGLITAZAR in patients with alcoholic hepatitis (AH), as determined by the absence of suspected unexpected serious adverse reaction (SUSAR).<br>2. Pharmacodynamic signals of INDEGLITAZAR: Model for End-Stage Liver Disease (MELD; Time Frame: 33 days) Drivers of the Model for End-Stage Liver Disease [MELD] score individually using a formula (3.78 × ln[serum bilirubin (mg/dL)] + 11.2 × ln[INR] + 9.57 × ln[serum creatinine (mg/dL)] + 6.43 that incorporates following lab measures: International Normalized Ratio [INR], and Serum Creatinine and Serum Total Bilirubin [units for both: mg/dl]) at baseline, Day 7 and Day 28. Participant's involvement in study: 33 days maximum.<br>3. Pharmacodynamic signals of INDEGLITAZAR: Liver Biochemical Biomarker "Alanine Aminotransferase" [Time Frame: 33 days.] |

TABLE 3-continued

Phase 2A Clinical Study of Indeglitazar in Human Alcoholic Hepatitis.

Protocol Synopsis: Phase 2A Proof of Concept

|  | |
|---|---|
| | Improvement in liver biochemistry at baseline, Day 7 and Day 28 (Alanine Aminotransferase [ALT, unit: IU/L]. Participant's involvement in study: 33 days maximum.<br>4. Pharmacodynamic signals of INDEGLITAZAR: Liver Biochemical Biomarker "Aspartate Aminotransferase" [Time Frame: 33 days.]<br>Improvement in liver biochemistry at baseline, Day 7 and Day 28 for Aspartate Aminotransferase [AST, unit: IU/L]. Participant's involvement in study: 33 days maximum.<br>5. Pharmacodynamic signals of INDEGLITAZAR: Liver Biochemical Biomarker "Total Bilirubin" [Time Frame: 33 days.]<br>Improvement in liver biochemistry at baseline, Day 7 and Day 28 for Total Bilirubin [unit: mg/dl]. Participant's involvement in study: 33 days maximum.<br>6. Pharmacodynamic signals of INDEGLITAZAR: Liver Biochemical Biomarker "Albumin" [Time Frame: 33 days.]<br>Improvement in liver biochemistry at baseline, Day 7 and Day 28 for Albumin [unit: g/L]. Participant's involvement in study: 33 days maximum.<br>7. Quality of life biomarkers: 36-item Short Form Survey (SF-36). [Time Frame: 33 days.] Quality of Life biomarkers (eg. SF-36) at Baseline, Day 7 and Day 28. Participant's involvement in study: 33 days maximum.<br>8. Biomarkers of liver cell death: Cytokeratin 18 (CK18) [Time Frame: 33 days.] Novel liver cell death markers: Cytokeratin18M65 (K18M65), and Cytokeratin18M30 (K18M30). Units: IU/L. Evaluation at baseline, day 7 and day 28. Participant's involvement in study: 33 days maximum.<br>9. Biomarkers of Inflammation (Interleukins): Interleukin 6, Interleukin 8, Interleukin 18 and Tumor Necrosis Factor a [Time Frame: 33 days.] interleukin 6 (IL6, unit: pg/mL), Interleukin 8 (IL8, unit: pg/mL), Interleukin 18 (IL18, unit: pg/ml) and Tumor Necrosis Factor $\alpha$ TNF $\alpha$, unit: pg/ml) at baseline, day 7 and day 28. Participant's involvement in study: 33 days maximum.<br>10. Biomarkers of Inflammation: C-reactive Protein [ Time Frame: 33 days.] C-reactive Protein (CRP, unit: mg/dL) assessed at baseline, day 7 and days 28. Participant's involvement in study: 33 days maximum.<br>11. Biomarkers of Inflammation: Adiponectin [Time Frame: 33 days.] Adiponectin (unit: µg/ml) assessed at baseline, day 7 and days 28. Participant's involvement in study: 33 days maximum.<br>12. ICU days? |
| Safety | Physical examination, vital signs, chemistry panel, CBC, urinalysis and ECG at each study visit; collection of follow-up adverse events and concomitant therapy at each study visit. Safety follow-up visit 4 weeks after last dose of study drug. |
| Sample Size | Statistical power estimated at 16 subjects per dose group (n = 3); a two-tailed P value of <0.05 will be required for statistical significance. Statistical methods will be documented in detail in the study analysis plan. The statistical analysis plan (SAP) will be reviewed and approved by the Sponsor prior to initiating of the study. |

Example 4. Evaluation of Indeglitazar in a Mouse Model of Human NAFLD, NASH, and Hepatic Fibrosis In this example, the efficacy of 1 daily dose (30 mg/kg body weight) of indeglitazar in a mouse (male) model of human NAFLD, NASH, and human hepatic fibrosis was evaluated. The objective of the examples is to evaluate the efficacy of indeglitazar (30 mg/kg/bw) on hepatic fibrosis and a validated biomarker for human hepatic fibrosis and validated biomarker of inflammation, using a previously described mouse model of human NAFLD, NASH, and hepatic fibrosis.

Materials and Methods

Mouse model generation and treatment. C57Bl/6 mice (6-week-old, males) were purchased from Jackson Laboratories and were housed under specific pathogen-free conditions. All experiment protocols were approved by the Institutional Animal Care and Use Committee (IACUC) of Pleiogenix, or its research partners. The mice were acclimated for a minimum of seven days prior to initiation of treatment (Sanyal A J et al., N Engl J Med, (2010), 362:1675-85). The mice were fed Purina normal chow and drinking water ad libitum during the acclimation period. After acclimation, the mice were randomized based on body weight (bw). A total of 22 mice were used; and treated as described in Table 1. Briefly, on day 0, mice were treated according to Table 4.

Liver fibrosis was induced as previously described (Nesto R W et al., Circulation, (2003), 108:2941-8). Carbon tetrachloride ($CCl_4$), formulated in mineral oil, was administered twice per week i.p. at 1 µl/gram body weight throughout the study duration (8 wks). Indeglitazar was administered daily by oral gavage at 30 mg/kg body weight throughout the study duration (8 wks). Mice were observed daily for clinical signs. Any observations noted outside of the scheduled observations were documented as unscheduled. Assessments included, but were not be limited to, assessment of activity, posture, respiration, emesis, seizure, hydration status, injection site irritation, and overall body condition. The absence or presence of findings were recorded.

Individual body weights were recorded on all animals prior to the initiation of the study and weekly body weights were recorded. Blood was collected and plasma was measured for alanine aminotransferase (ALT) and aspartate aminotransferase (AST) and on weeks 0 (baseline), 4, and wk 8 (terminal). At the end of the study, liver necropsy was performed including weighing and processing for histology, and frozen at −80° C. for the following downstream analyses: Liver histopathology: hematoxyline and eosin (H&E) staining (Kumar P et al., PLOS ONE, (2014), 9:e110405); Sirius Red staining for fibrosis (Nesto R W et al., Circulation, (2003), 108:2941-8). Biochemical markers of human hepatic fibrosis and anti-fibrotic adipokine, adiponectin: hepatic hydroxyproline (Nesto R W et al., Circulation, (2003), 108:2941-8); plasma TGFβ1 (Fischer A H et al., CSH Protoc, (2008), 2008:pdb.prot4986); adiponectin (Guo J C et al., Zhonghua Shi Yan He Lin Chuang Bing Du Xue Za Zhi, (2008), 22:354-7).

TABLE 4

Study Groups

| Group # | Mice (Males) | Indeglitazar (mg/kg bw) | Diet (Day 6-12) | $CCl_4$ |
|---|---|---|---|---|
| 1 | 5 | 0 | Purina chow diet without $CCl_4$ | Day 12 |
| 2 | 8 | 0 | LCD diet with ethanol plus indeglitazar by oral gavage | Day 12 |
| 3 | 9 | 30 | Purina chow diet with $CCl_4$ plus indeglitazar by oral gavage | Throughout experiment |

Table 4. Study groups. Indeglitazar dose was selected on the basis of previous experiments conducted in a methionine-chloride-deficient diet mouse model of NASH (Takahashi Y et al., Animal Models for the Study of Human Disease (Second Edition): Academic Press, (2017), p. 313-39).

Analysis and tests: Mice were treated for 11 days; body weights were measured before and during administration. Plasma was analyzed for ALT, AST, and GGT. A full necropsy was performed at the end-point together with liver histology to assess steatosis, and inflammatory infiltrates. Briefly, liver tissue was fixed in 10% neutral buffered formalin and paraffin-embedded, sectioned into 5 m thickness, and stained with hematoxylin-eosin (H&E) and Oil-Red O staining for evaluation of histopathological changes. Stained liver slices were analyzed under a bright-field microscope using the histological scoring system for non-alcoholic fatty liver disease (Kleiner D E et al., Hepatology, (2005), 41:1313-21). The remaining liver tissue was analyzed for liver triglycerides and cholesterol levels by biochemical assays.

Results

Figure 11:
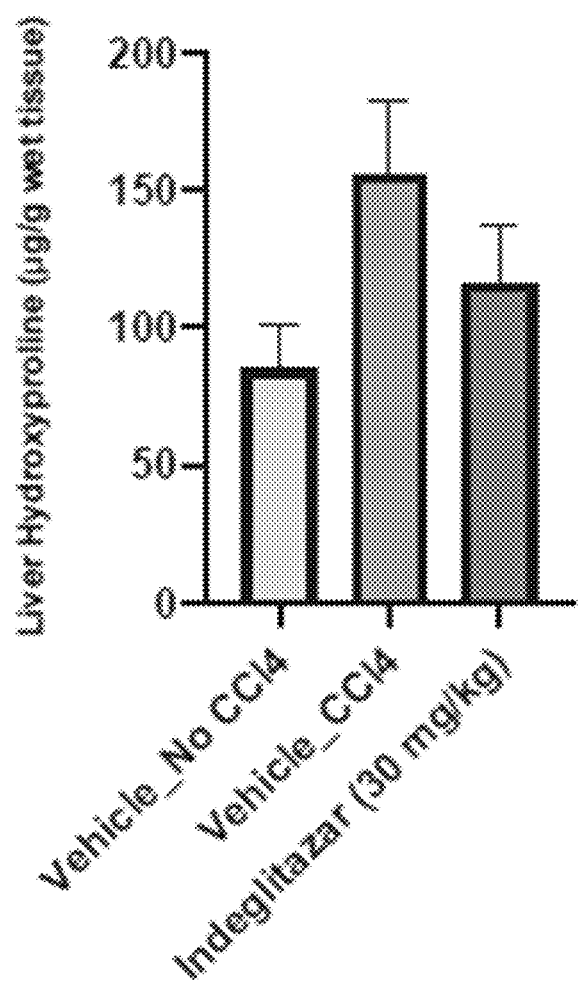
FIG. 11. A single dose (30 mg/kg/day) of indeglitazar showing that indeglitazar significantly reduces liver hydroxyproline, a validated biomarker of liver fibrosis, in the carbon tetrachloride ($CCl_4$)-treated mice (male mice) model of human NAFLD, NASH, and hepatic fibrosis described in Example 4.
Figure 12:
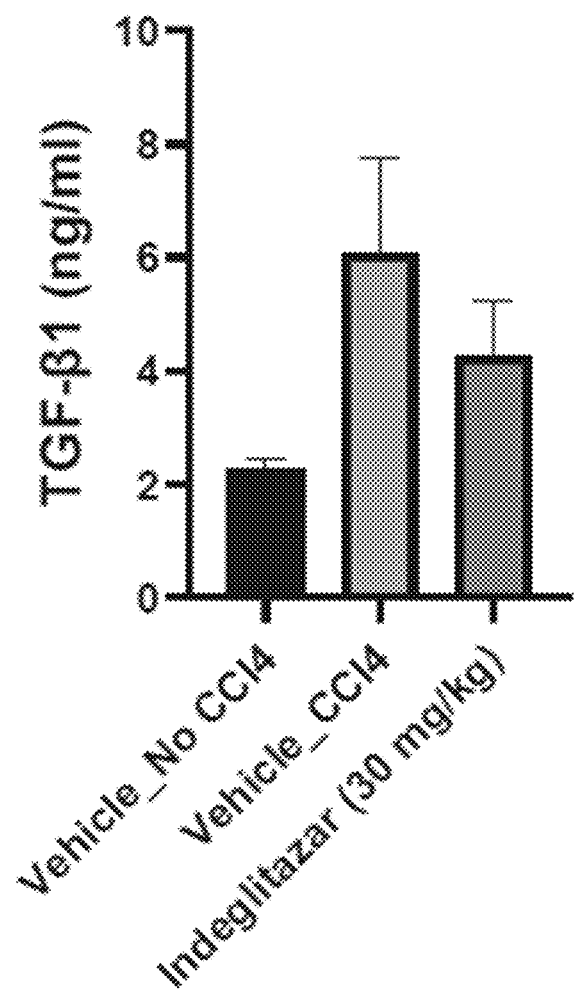
FIG. 12. A single dose (30 mg/kg/day) of indeglitazar showing that indeglitazar significantly reduces plasma transforming growth factor-β1 (TGF-β1), a validated biomarker of liver fibrosis, in the $CCl_4$-treated mice (male mice) model of human NAFLD, NASH, and hepatic fibrosis described in Example 4.
Figure 13:
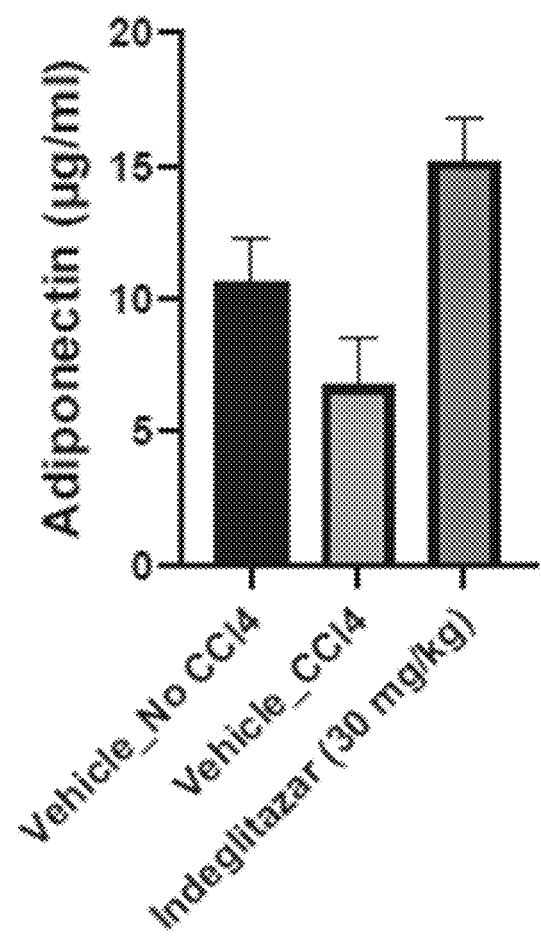
FIG. 13. A single dose (30 mg/kg/day) of indeglitazar showing that indeglitazar significantly increases plasma adiponectin, a beneficial biomarker of liver steatosis and fibrosis, in the $CCl_4$-treated mice (male mice) model of human NAFLD, NASH, and hepatic fibrosis described in Example 4.

Results are depicted in FIGS. 11-13, and summarized as follows: In vehicle-treated mice, $CCl_4$ treatment caused a significant increase in liver hydroxyproline, a validated index of hepatic fibrosis (FIG. 11). A single dose (30 mg/kg/day) of indeglitazar significantly reduced liver hydroxyproline in the carbon tetrachloride ($CCl_4$)-treated mice model of human NAFLD and NASH and human hepatic fibrosis, compared to the $CCl_4$ vehicle treatment (FIG. 11).

In vehicle-treated mice, $CCl_4$ treatment caused a significant increase in plasma TGFβ1, a validated biomarker of fibrosis (FIG. 12). A single dose (30 mg/kg/day) of indeglitazar significantly reduced plasma TGFβ1 in the carbon tetrachloride ($CCl_4$)-treated mice model of human NAFLD and NASH and human hepatic fibrosis, compared to the $CCl_4$ vehicle treatment (FIG. 12).

In vehicle-treated mice, $CCl_4$ treatment caused a significant decrease in plasma adiponectin, a validated biomarker of inflammation (FIG. 13). A single dose (30 mg/kg/day) of indeglitazar significantly increased plasma adiponectin in the carbon tetrachloride ($CCl_4$)-treated mice model of human NAFLD and NASH and human hepatic fibrosis described in Example 1, compared to the $CCl_4$ vehicle treatment (FIG. 13).

Conclusion

Indeglitazar produced a significant beneficial effect on reducing hepatic fibrosis, as judged by a reduction in hydroxyproline, a validated indicator of hepatic fibrosis. The magnitude of the reduction was approximately 25%. Indeglitazar also produced a significant beneficial effect on reducing plasma TGFβ1. The magnitude of the reduction was approximately 30%. Indeglitazar also produced a significant beneficial effect on increasing plasma adiponectin. The magnitude of the increase was approximately 125%. Increased adiponectin is beneficial in NAFLD, NASH, alcoholic hepatitis, and human hepatic fibrosis, since it is anti-fibrotic and facilitates fat-burning in the liver.

Example 5. Evaluation of Indeglitazar for Alcoholic Hepatitis

Indeglitazar demonstrates efficacy benefits, including reduced fibrosis, increased survival, and lack of safety concerns, in an NIAAA mouse model of chronic alcohol exposure. Indeglitazar exhibited superiority versus the clinical standard of care for human AH (i.e., prednisolone).

Summary of Blood-Brain Barrier Assessment

Indeglitazar has been evaluated for the ability to pass through the blood-brain-barrier, and has demonstrated adequate permeability. Indeglitazar was evaluated using the Parallel Artificial Membrane Permeability-Blood Brain Barrier Assay (PMBBB-096; BioAssay Systems, Hayward, CA). Compared to promazine HCl (high permeability control), indeglitazar exhibits an approximate 15% ability to cross the blood-brain barrier.

Additional Studies

The AH mouse model was generated as described in Shah et al. through chronic and binge ethanol (EtOH) feeding plus lipopolysaccharide (LPS) administration, to provide a second insult, to increase liver damage (Bertola A et al., *Nat Protoc*, (2013), 8:627-637; Takahashi Y et al., (2017), 313-339; Shah R et al., *Oxid Med Cell Longev*, (2018), 2018: 9630175). This model recapitulates the major features of human AH, including marked ALT and AST elevation, liver steatosis, and fibrosis (Lucey M R et al., *N Engl J Med.*, (2009), 360:2758-2769). For a dose-response study, a total of 60 (12 per group, 50:50 male/female ratio) C57BL6 mice (6-8-weeks old) were fed Lieber-DeCarli '82 rodent liquid diet (LDC) ad libitum, for 5 days, to acclimatize them to tube feeding. On days 6-11, mice were fed the LCD diet plus ethanol (5% vol:vol), and treated with indeglitazar (10 mg/kg, 30 mg/kg, or 50 mg/kg, oral gavage). On day 12, mice were given a single dose of EtOH (5 g/kg/body weight) by oral gavage and LPS (2 mg/kg/body weight) by ip injection; pair-fed mice were fed isocaloric maltose dextrin and all mice were euthanized 6 h later. LDC diet consumption was monitored daily to ensure that indeglitazar did not affect food intake.

For a one month efficacy and safety study, 100 mice (10 per group, 50:50 male/female ratio) were fed with the LDC diet plus EtOH (5% vol:vol) for 4 weeks, followed by 4 weeks of intervention, including maintenance on the EtOH diet. The 5 experimental groups were 1) LCD diet minus EtOH; 2) LCD diet plus EtOH; LCD diet plus EtOH and the following interventions: 3) indeglitazar (50 mg/kg); 4) prednisolone (10 mg/kg); 5) indeglitazar (50 mg/kg)+prednisolone (10 mg/kg).

Dose-response of indeglitazar in AH mouse model. The efficacy of 3 daily doses (10, 30, and 50 mg/kg) of orally administered (by gavage) indeglitazar in the NIAAA mouse model was evaluated for days 6-11. Neither EtOH (vs no EtOH vehicle control) or indeglitazar had a significant effect on body weight or food intake, compared to the EtOH-treated vehicle control, at any dose evaluated (P>0.05; data not shown). In vehicle-treated mice, EtOH treatment caused a significant increase in the enzyme activity of ALT (P<0.0001; FIG. 14). Each dose of indeglitazar caused a significant decrease in ALT activity compared to the EtOH-treated vehicle control group. Indeglitazar (50 mg/kg) reduced ALT activity by 60% vs vehicle+EtOH (P<0.0001; FIG. 14). EtOH treatment caused a significant increase (vs no EtOH vehicle group) in the enzyme activity of AST (P<0.0002; FIG. 14). Indeglitazar (10 and 50 mg/kg) caused significant decreases in AST activity compared to the EtOH-treated vehicle control group. Indeglitazar (50 mg/kg) reduced AST by 49% vs vehicle+EtOH (P<0.004; FIG. 14). In vehicle-treated mice, EtOH treatment caused a significant increase in liver triglycerides (TG; P<0.0005; FIG. 14). Indeglitazar (50 mg/kg) significantly reduced liver TG, a marker of hepatic steatosis, by 35% vs vehicle+EtOH (P<0.03; FIG. 14). Based on this dose-response assessment, the 50 mg/kg body weight per day dose of indeglitazar was selected for further evaluation, in the 30-day study.

Indeglitazar (50 mg/kg) is superior to prednisolone treatment. Neither EtOH (vs no EtOH vehicle control), indeglitazar, or prednisolone had a significant effect on body or heart weights, compared to the EtOH-treated vehicle control (P>0.05; data not shown). FIG. 15 and Table 5 indicate the effects of indeglitazar alone and in combination with prednisolone on ALT, AST, bilirubin, adiponectin, liver TG, and liver hydroxyproline (marker of liver fibrosis). In vehicle-treated mice, EtOH treatment caused significant increases in the activities of ALT and AST and bilirubin. Indeglitazar caused significant decreases in ALT, AST, and bilirubin, compared to the ethanol-treated vehicle control group (alone and in combination with prednisolone). Prednisolone had no significant effect on ALT, AST, but increased bilirubin (FIG. 15). In vehicle-treated mice, ethanol treatment had no significant effect on plasma adiponectin (FIG. 16; Table 5). Indeglitazar caused a significant increase in adiponectin compared to the EtOH-treated vehicle control group, alone and in combination with prednisolone (FIG. 16; Table 5). Indeglitazar increased adiponectin by 31% vs vehicle+EtOH (P<0.0001). Indeglitazar and prednisolone increased adiponectin by 44% vs vehicle+EtOH (P<0.0001). Prednisolone had no significant effect on adiponectin (+3.4% vs vehicle+EtOH (P>0.05; FIG. 16; Table 5). In vehicle-treated mice, EtOH treatment caused a significant increase in liver TG (P<0.0001; Table 5). Indeglitazar decreased liver TG by 28% vs vehicle+EtOH (P<0.003; indeglitazar and prednisolone decreased liver TG by 23% vs vehicle+EtOH (P<0.02). Prednisolone had no significant effect on liver triglycerides (Table 5). In vehicle-treated mice, EtOH treatment caused a significant increase in liver hydroxyproline (P<0.0008; Table 5). Indeglitazar caused a significant decrease in liver hydroxyproline compared to the EtOH-treated vehicle control group, both alone and in combination with prednisolone (Table 5). Indeglitazar decreased hydroxyproline by 31% vs vehicle+EtOH (P<0.0001; Table 5). Indeglitazar and prednisolone decreased hydroxyproline by 23% vs vehicle+EtOH (P<0.0001; Table 5).

TABLE 5

Effects of Indeglitazar on ALT, AST, adiponectin, hepatic triglycerides, and hepatic hydroxyproline.

| Parameter | Vehicle, No EtOH | Vehicle + EtOH | PLG888 (50 mg/kg) | Prednisolone (10 mg/kg) | PLG888 (50 mg/kg) + Prednisolone (10 mg/kg) |
| --- | --- | --- | --- | --- | --- |
| ALT (U/L) | 35.90 ± 1.65 | 541.1 ± 198.6 | 223.9 ± 96.80 | 439.6 ± 153.5 | 159.8 ± 70.53 |
| AST (U/L) | 102.3 ± 33.09 | 585.2 ± 193.3 | 252.1 ± 84.86 | 537.6 ± 180.0 | 265.1 ± 66.18 |
| Adiponectin (µg/ml) | 13.30 ± 2.222 | 14.43 ± 1.022 | 18.95 ± 1.564 | 14.92 ± 1.241 | 20.73 ± 1.603 |
| Hepatic Triglycerides (mg/dL) | 23.95 ± 6.476 | 53.58 ± 15.19 | 38.40 ± 5.452 | 48.50 ± 16.98 | 41.32 ± 11.49 |
| Hepatic Hydroxyproline (µg/g wet tissue) | 85.63 ± 15.96 | 110.5 ± 20.95 | 76.73 ± 4.08 | 103.1 ± 8.157 | 84.63 ± 11.70 |

Prednisolone had no significant effect on hydroxyproline vs vehicle+EtOH (−7%; P>0.05). In vehicle-treated mice, EtOH treatment significantly increased plasma TGFβ (P<0.0001; FIG. 16). Indeglitazar caused a significant decrease in plasma TGFβ compared to the ethanol-treated vehicle control group, alone and in combination with prednisolone (FIG. 16). Indeglitazar decreased TGFβ by 66% vs vehicle+EtOH (P<0.0001). Indeglitazar and prednisolone decreased plasma TGFβ by 52% vs vehicle+EtOH (P<0.0003; FIG. 16). Prednisolone decreased TGFβ by 56% vs vehicle+EtOH (P<0.001; FIG. 16). In vehicle-treated mice, ethanol treatment significantly increased plasma TNF-α (P<0.0001; FIG. 16). Indeglitazar decreased plasma TNF-α by 50% vs vehicle+EtOH (P<0.04; FIG. 16). Indeglitazar plus prednisolone protected against the prednisolone-mediated increase in plasma TNF-α by reducing plasma TNF-α by 24% vs vehicle+EtOH (P>0.05; FIG. 16). Prednisolone increased plasma TNF-α by 123% vs vehicle+EtOH (P<0.0001; FIG. 16). The histopathological analyses of liver samples showed that steatosis, hepatocellular karyomegaly, and ballooning were reduced significantly in Indeglitazar-treated mice (data not shown). Prednisolone had no significant effect on these parameters.

Indeglitazar increases survival in NIAAA mouse model. In vehicle-treated mice, ethanol treatment caused a significant decrease in overall survival (P<0.002; data not shown). In our protocol, 10 male and 10 female mice were exposed to alcohol for a total of 8 weeks: 4 weeks prior to treatment with test compounds and 4 weeks while being treated with test compounds. The mortality rate in our alcohol-vehicle group was 40%: 8 of 20 mice died (3 males, 5 females). Neither EtOH (vs no EtOH vehicle control), indeglitazar, or prednisolone had a significant effect on body or heart weights, compared to the EtOH-treated vehicle control (P>0.05; data not shown). Indeglitazar caused a significant increase in overall survival compared to the EtOH-treated vehicle control group, both alone (P<0.002; FIG. 17) and in combination with prednisolone (P<0.002; FIG. 17). Prednisolone had no significant effect on overall survival time (P>0.05; FIG. 17), compared to the ethanol-treated vehicle control group. These studies provide strong evidence regarding the efficacy of indeglitazar (50 mg/kg body weight/day) in the NIAAA mice. Specifically, indeglitazar improved validated markers of liver function (ALT, AST, bilirubin), fibrosis (hydroxyproline, adiponectin), steatosis (liver triglycerides, histopathological score), inflammation (adiponectin, TGFβ, TNF-α), along with the histopathological scores for steatosis, hepatocellular karyomegaly, and ballooning. Most importantly, indeglitazar significantly increased the overall survival of male and female mice, chronically exposed to ethanol, when administered alone or in combination with prednisolone.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method of treating alcoholic hepatitis in a subject, comprising administering to the subject a therapeutically effective amount of indeglitazar or a pharmaceutically acceptable salt thereof.

2. The method of claim 1, wherein the treatment results in an improvement in a fibrosis marker selected from TIMP-1, TIMP-2, hyaluronic acid, P3NP, NFS, FIB-4 score, ELF score, Pro-C3, and combinations thereof.

3. The method of claim 1, wherein the treatment results in a reduction of alanine aminotransferase (ALT) activity in liver of at least 50%.

4. The method of claim 1, wherein the treatment results in a reduction of the fibrosis marker hepatic hydroxyproline of at least 25%.

5. The method of claim 1, wherein the treatment results in a reduction in the marker bilirubin of at least 15%.

6. The method of claim 1, wherein the treatment results in a reduction in plasma TGF-β1 of at least 25%.

7. The method of claim 1, wherein the treatment results in a reduction in plasma TNF-α of at least 25%.

8. The method of claim 1, wherein the treatment results in a reduction of liver triglycerides of at least 15%.

9. The method of claim 1, wherein the treatment results in an increase in plasma adiponectin of at least 100%.

10. The method of claim 1, wherein the treatment results in a reduction of alanine aminotransferase (AST) activity in liver of at least 50%.

11. The method of claim 1, wherein the subject does not have type 2 diabetes.

12. The method of claim 1, wherein hepatocellular karyomegaly is reduced in the subject following treatment.

13. The method of claim 1, wherein hepatocyte ballooning is reduced in the subject following treatment.

14. The method of claim 1, wherein the treatment results in an improvement in levels of fibrinogen, hsCRP, alpha2 macroglobulin, haptoglobin, or a combination thereof.

15. The method of claim 1, wherein the subject has a BMI greater than 30.

16. The method of claim 1, wherein the subject has an F1 grade of fibrosis.

17. The method of claim 1, wherein the therapeutically effective amount of indeglitazar comprises about 50 mg/day or about 100 mg/day.

18. The method of claim 1, wherein indeglitazar is administered orally.

19. The method of claim 1, wherein the subject is administered one or more additional therapeutically active agents.

20. The method of claim 19, wherein the one or more additional therapeutically active agents is selected from prednisolone, pentoxifylline, and a combination thereof.

21. The method of claim 1, wherein the method results in an improvement in NASH CRN fibrosis score.

22. The method of claim 1, further comprising administering an effective amount of resmetirom to the subject.

* * * * *